US012799475B2

(12) United States Patent
Adey et al.

(10) Patent No.: US 12,799,475 B2
(45) **Date of Patent: *Nov. 17, 2026**

(54) SINGLE CELL WHOLE GENOME LIBRARIES FOR METHYLATION SEQUENCING

(71) Applicants: OREGON HEALTH & SCIENCE UNIVERSITY, Portland, OR (US); ILLUMINA, INC., San Diego, CA (US)

(72) Inventors: Andrew C. Adey, Portland, OR (US); Ryan Mulqueen, Portland, OR (US); Frank J. Steemers, San Diego, CA (US); Dmitry K. Pokholok, San Diego, CA (US); Steven Norberg, San Diego, CA (US)

(73) Assignees: OREGON HEALTH & SCIENCE UNIVERSITY, Portland, OR (US); ILLUMINA, INC., San Diego, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/000,505

(22) Filed: Jun. 5, 2018

(65) Prior Publication Data

US 2018/0355348 A1 Dec. 13, 2018

Related U.S. Application Data

(60) Provisional application No. 62/516,324, filed on Jun. 7, 2017.

(51) Int. Cl.

| | |
|---|---|
| ***C12N 15/10*** | (2006.01) |
| ***C12Q 1/6806*** | (2018.01) |
| *C12Q 1/6874* | (2018.01) |
| *C40B 50/18* | (2006.01) |

(52) U.S. Cl.

CPC ....... *C12N 15/1065* (2013.01); *C12Q 1/6806* (2013.01); *C12N 15/1093* (2013.01); *C12Q 1/6874* (2013.01); *C12Q 2523/125* (2013.01); *C40B 50/18* (2013.01)

(58) Field of Classification Search

CPC ............ C12N 15/1065; C12N 15/1093; C12Q 1/6806; C12Q 2523/125; C12Q 1/6874; C12Q 2525/191; C12Q 2537/159; C12Q 2563/179; C40B 50/18

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,130,238 | A | 7/1992 | Malek et al. |
| 5,185,243 | A | 2/1993 | Ullman et al. |
| 5,223,414 | A | 6/1993 | Zarling et al. |
| 5,455,166 | A | 10/1995 | Walker |
| 5,573,907 | A | 11/1996 | Carrino et al. |
| 5,679,524 | A | 10/1997 | Nikiforov et al. |
| 6,172,218 | B1 | 1/2001 | Brenner |
| 6,210,891 | B1 | 4/2001 | Nyren et al. |
| 6,214,587 | B1 | 4/2001 | Dattagupta et al. |
| 6,245,974 | B1 | 6/2001 | Michalowski et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,514,706 | B1 | 2/2003 | Von Kalle et al. |
| 6,699,666 | B1 | 3/2004 | Yoshimi et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,399,590 | B2 | 7/2008 | Piepenburg et al. |
| 7,405,281 | B2 | 7/2008 | Xu et al. |
| 7,427,673 | B2 | 9/2008 | Balasubramanian et al. |
| 7,582,420 | B2 | 9/2009 | Oliphant et al. |
| 7,611,869 | B2 | 11/2009 | Fan |
| 7,741,463 | B2 | 6/2010 | Gormley et al. |
| 7,829,284 | B2 | 11/2010 | Kong et al. |
| 7,910,354 | B2 | 3/2011 | Drmanac et al. |
| 8,003,354 | B2 | 8/2011 | Shen et al. |
| 8,053,192 | B2 | 11/2011 | Bignell et al. |

(Continued)

FOREIGN PATENT DOCUMENTS

| | | |
|---|---|---|
| CN | 103890191 A | 6/2014 |
| CN | 105339503 A | 2/2016 |

(Continued)

OTHER PUBLICATIONS

Vitak et al. (BioRxiv (2016): 065482; 18 pages; published Jul. 23, 2016) (Year: 2016).*
Amini et al. (Nature genetics 46.12 (2014): 1343) (Year: 2014).*
Amini 2014 supplementary information (Year: 2014).*
Wang et al. (Nature protocols 8.10 (2013): 2022-2032.) (Year: 2013).*
Smallwood et al. (Nature methods 11.8 (2014): 817-820.) (Year: 2014).*
Adey and Shendure, "Ultra-low-input, tagmentation-based whole-genome bisulfite sequencing," Genome Research (Mar. 30, 2012), 22:1139-1143. (Year: 2012).*

(Continued)

*Primary Examiner* — Jeremy C Flinders
*Assistant Examiner* — Alexandra Olson
(74) *Attorney, Agent, or Firm* — Mueting Raasch Group

(57) ABSTRACT

Provided herein are methods for preparing sequencing libraries for determining the methylation status of nucleic acids from a plurality of single cells. The present methods combine split-and-pool combinatorial indexing and bisulfite treatment techniques to characterize the methylation profiles of large numbers of single cells quickly, accurately and inexpensively.

16 Claims, 6 Drawing Sheets

Specification includes a Sequence Listing.

(56) References Cited

U.S. PATENT DOCUMENTS

| | | | |
|---|---|---|---|
| 8,563,477 | B2 | 10/2013 | Smith et al. |
| 8,778,848 | B2 | 7/2014 | Lin et al. |
| 8,778,849 | B2 | 7/2014 | Bowen et al. |
| 8,895,249 | B2 | 11/2014 | Shen et al. |
| 8,951,781 | B2 | 2/2015 | Reed et al. |
| 9,079,148 | B2 | 7/2015 | Rigatti et al. |
| 9,169,513 | B2 | 10/2015 | Shen et al. |
| 9,309,502 | B2 | 4/2016 | Piepenburg et al. |
| 9,359,642 | B2 | 6/2016 | Yin et al. |
| 10,900,065 | B2 | 1/2021 | Seelig et al. |
| 11,168,355 | B2 | 11/2021 | Seelig et al. |
| 11,427,856 | B2 | 8/2022 | Seelig et al. |
| 11,535,883 | B2 | 12/2022 | Adey et al. |
| 2005/0079516 | A1 | 4/2005 | Maniotis et al. |
| 2005/0100900 | A1 | 5/2005 | Mayer et al. |
| 2005/0272070 | A1 | 12/2005 | Mathias et al. |
| 2006/0188901 | A1 | 8/2006 | Barnes et al. |
| 2006/0240439 | A1 | 10/2006 | Smith et al. |
| 2006/0281109 | A1 | 12/2006 | Ost et al. |
| 2007/0099208 | A1 | 5/2007 | Drmanac et al. |
| 2007/0166705 | A1 | 7/2007 | Milton et al. |
| 2008/0009420 | A1 | 1/2008 | Schroth et al. |
| 2008/0108082 | A1 | 5/2008 | Rank et al. |
| 2009/0005252 | A1 | 1/2009 | Drmanac et al. |
| 2009/0011943 | A1 | 1/2009 | Drmanac et al. |
| 2009/0026082 | A1 | 1/2009 | Rothberg et al. |
| 2009/0047680 | A1 | 2/2009 | Lok |
| 2009/0118488 | A1 | 5/2009 | Drmanac et al. |
| 2009/0127589 | A1 | 5/2009 | Rothberg et al. |
| 2009/0155781 | A1 | 6/2009 | Drmanac et al. |
| 2009/0264299 | A1 | 10/2009 | Drmanac et al. |
| 2010/0111768 | A1 | 5/2010 | Banerjee et al. |
| 2010/0120098 | A1 | 5/2010 | Grunenwald et al. |
| 2010/0137143 | A1 | 6/2010 | Rothberg et al. |
| 2010/0282617 | A1 | 11/2010 | Rothberg et al. |
| 2011/0287435 | A1 | 11/2011 | Grunenwald et al. |
| 2012/0094849 | A1 | 4/2012 | Rava et al. |
| 2012/0208705 | A1 | 8/2012 | Steemers et al. |
| 2012/0208724 | A1 | 8/2012 | Steemers et al. |
| 2012/0270305 | A1 | 10/2012 | Reed et al. |
| 2013/0079232 | A1 | 3/2013 | Kain et al. |
| 2013/0184796 | A1 | 7/2013 | Marzano et al. |
| 2013/0196860 | A1 | 8/2013 | Grunenwald et al. |
| 2013/0260372 | A1 | 10/2013 | Buermann et al. |
| 2013/0338042 | A1 | 12/2013 | Shen et al. |
| 2014/0194313 | A1 | 7/2014 | Craighead et al. |
| 2014/0194324 | A1 | 7/2014 | Gormley et al. |
| 2014/0200146 | A1 | 7/2014 | Xie et al. |
| 2014/0243224 | A1 | 8/2014 | Barnard et al. |
| 2014/0274740 | A1 | 9/2014 | Srinivasan et al. |
| 2015/0011396 | A1* | 1/2015 | Schroeder .......... C12N 15/1093 506/26 |
| 2015/0329891 | A1 | 11/2015 | Tan et al. |
| 2015/0337298 | A1 | 11/2015 | Xi et al. |
| 2016/0060691 | A1 | 3/2016 | Giresi et al. |
| 2016/0061517 | A1 | 3/2016 | Seitter et al. |
| 2017/0342483 | A1* | 11/2017 | Arezi ................. C12N 15/1065 |
| 2018/0023119 | A1 | 1/2018 | Adey et al. |
| 2018/0273933 | A1 | 9/2018 | Gunderson et al. |
| 2018/0340172 | A1 | 11/2018 | Belhocine et al. |
| 2018/0355348 | A1 | 12/2018 | Adey et al. |
| 2019/0040382 | A1 | 2/2019 | Steemers et al. |
| 2019/0071656 | A1 | 3/2019 | Chang et al. |
| 2019/0382753 | A1 | 12/2019 | Steemers et al. |

FOREIGN PATENT DOCUMENTS

| | | | | |
|---|---|---|---|---|
| EP | 320308 | B1 | 11/1993 | |
| EP | 336731 | B1 | 5/1994 | |
| EP | 439182 | B1 | 4/1996 | |
| JP | H08239400 | A | 9/1996 | |
| JP | 2007526743 | A | 9/2007 | |
| JP | 2010535513 | A | 11/2010 | |
| JP | 2015519084 | A | 7/2015 | |
| JP | 2016508715 | A | 3/2016 | |
| JP | 2016518860 | A | 6/2016 | |
| JP | 2017-506877 | A | 3/2017 | |
| JP | 2020-523011 | A1 | 6/2020 | |
| KR | 20170107423 | A | 9/2017 | |
| RU | 2529784 | C2 | 9/2013 | |
| RU | 2571855 | | 12/2014 | |
| RU | 2571855 | C2 | 12/2015 | |
| WO | 8703910 | A1 | 7/1987 | |
| WO | 8909835 | A1 | 10/1989 | |
| WO | 8912696 | A1 | 12/1989 | |
| WO | 9001069 | A1 | 2/1990 | |
| WO | 9106678 | A1 | 5/1991 | |
| WO | 9523875 | A1 | 9/1995 | |
| WO | 9844151 | A1 | 10/1998 | |
| WO | WO 00/17339 | A1 | 3/2000 | |
| WO | 0018957 | A1 | 4/2000 | |
| WO | 0246456 | A1 | 6/2002 | |
| WO | 2004018497 | A2 | 3/2004 | |
| WO | 2004108951 | A1 | 12/2004 | |
| WO | 2005065814 | A1 | 7/2005 | |
| WO | 2006064199 | A1 | 6/2006 | |
| WO | 2007010251 | A2 | 1/2007 | |
| WO | 2007123744 | A2 | 11/2007 | |
| WO | 2012061832 | A1 | 5/2012 | |
| WO | 2013188582 | A1 | 12/2013 | |
| WO | 2014142850 | A1 | 9/2014 | |
| WO | WO-2014145820 | A2 * | 9/2014 | ........... C12Q 1/6806 |
| WO | 2014189957 | A2 | 11/2014 | |
| WO | 2015002813 | A1 | 1/2015 | |
| WO | 2015/026853 | A2 | 2/2015 | |
| WO | 2015106941 | A1 | 7/2015 | |
| WO | WO 2015/103339 | A1 | 7/2015 | |
| WO | WO-2015104302 | A1 * | 7/2015 | ......... C12N 15/1093 |
| WO | 2016003814 | A1 | 1/2016 | |
| WO | WO 2016/061517 | A2 | 4/2016 | |
| WO | 2016066586 | A1 | 5/2016 | |
| WO | 2016083823 | A1 | 6/2016 | |
| WO | WO 2016/126871 | A2 | 8/2016 | |
| WO | WO 2016/130704 | A2 | 8/2016 | |
| WO | 2018018008 | A1 | 1/2018 | |
| WO | WO 2018/226708 | A1 | 12/2018 | |
| WO | 2019222688 | A1 | 11/2019 | |

OTHER PUBLICATIONS

International Search Report and Written Opinion for PCT/US2018/036078 mailed on Sep. 18, 2018, 14 pages.

Adey and Shendure, "Ultra-low-input, tagmentation-based whole-genome bisulfite sequencing," *Genome Res.*, Mar. 30, 2012; 22:1139-43.

Angermueller et al. "Parallel single-cell sequencing links transcriptional and epigenetic heterogeneity," *Nat Methods.*, Mar. 2016; 13(3):229-232.

Clark et al., "Single-cell epigenomics: powerful new methods for understanding gene regulation and cell identity," *Genome Biol.*, Apr. 18, 2016; 17(72):1-10.

Cusanovich et al., "Multiplex single-cell profiling of chromatin accessibility by combinatorial cellular indexing," *Science*, May 7, 2015; 348(6237):910-914.

Devarajan, "Nonnegative Matrix Factorization: An Analytical and Interpretive Tool in Computational Biology," *PLoS Comput Biol.*, Jul. 25, 2008; 4(7):e1000029.

Diep et al., "Library-free Methylation Sequencing with Bisulfite Padlock Probes," *Nat. Methods.*, Sep. 30, 2012; 9(3):270-272.

Farlik et al., "DNA Methylation Dynamics of Human Hematopoietic Stem Cell Differentiation," *Cell Stem Cell.*, Dec. 1, 2016; 19(6):808-822.

Farlik et al., "Single-Cell DNA Methylome Sequencing and Bioinformatic Inference of Epigenomic Cell-State Dynamics," *Cell Reports*, Mar. 3, 2015; 10:1386-1397.

Frommer et al., "A genomic sequencing protocol that yields a positive display of 5-methylcytosine residues in individual DNA strands," *Proc. Natl. Acad. Sci. USA*, Mar. 1, 1992; 89(5):1827-1831.

(56) References Cited

OTHER PUBLICATIONS

Gravina et al., "Single-cell genome-wide bisulfite sequencing uncovers extensive heterogeneity in the mouse liver methylome," *Genome Biology,* 2016; 17:150, 1-8.
Grothues et al., "PCR amplification of megabase DNA with tagged random primers (T-PCR)," *Nucleic Acids Res.,* Mar. 11, 1993; 21(5):1321-2.
Harvey and Cheng, "Methods for Characterization of Alternative RNA Splicing," In: Feng Y., Zhang L. (eds) Long Non-Coding RNAs. Methods in Molecular Biology, vol. 1402, 2016, 229-241. https://doi.org/10.1007/978-1-4939-3378-5_18.
Hu et al., "Simultaneous profiling of transcriptome and DNA methylome from a single cell," *Genome Biol.,* 2016; 17:88, 1-11.
Jamieson et al., "Exploring nonlinear feature space dimension reduction and data representation in breast CADx with Laplacian eigenmaps and t-SNE," *Med. Phys.,* Jan. 2010; 37(1):339-351.
Krueger and Andrews et al., "Bismark: a flexible aligner and methylation caller for Bisulfite-Seq applications," Jun. 1, 2011; 27(11):1571-1572.
Lister et al., "Global Epigenomic Reconfiguration During Mammalian Brian Development," *Science,* Aug. 9, 2013, Epub Jul. 4, 2013; 341(6146):1237905.
Olek et al., "A modified and improved method for bisulphite based cytosine methylation analysis," *Nucleic Acids Res.,* Dec. 15, 1996; 24(24):5064-6.
Pollen et al., "Low-coverage single-cell mRNA sequencing reveals cellular heterogeneity and activated signaling pathways in developing cerebral cortex," *Nat. Biotechnol.,* Oct. 2014, Epub Aug. 3, 2014; 32(10):1053-1058.
Ruiz et al., "Identification of a specific reprogramming-associated epigenetic signature in human induced pluripotent stem cells," *Proc Natl Acad Sci USA,* Oct. 2, 2012, Epub Sep. 18, 2012; 109(40):16196-201. (2012).
Smallwood et al., "Single-cell genome-wide bisulfite sequencing for assessing epigenetic heterogeneity," *Nature Methods,* Aug. 1, 2014; 11(8):817-822.
Svensson et al., "Power analysis of single-cell RNA-sequencing experiments," *Nat. Methods,* Apr. 2017, Epub Mar. 6, 2017; 14(4):381-387.
Vester and Wengel, "LNA (Locked Nucleic Acid): High-Affinity Targeting of Complementary RNA and DNA," *Biochemistry,* Oct. 26, 2004; 43(42):13233-41.
Vitak et al., "Sequencing thousands of single-cell genomes with combinatorial indexing," *Nature Methods,* Jan. 30, 2017; 14(3):302-311.
Zerbino et al., "The Ensembl Regulatory Build," *Genome Biol.,* Mar. 24, 2015; 16:56.
International Search Report and Written Opinion for International Application No. PCT/US2019/032966, Sep. 20, 2019, 13 pages.
Cao et al., "Comprehensive Single-cell transcriptional profiling of a multicellular organism," *Science,* 2017; 357:661-667.
Cao et al., "The single-cell transcriptional landscape of mammalian organogenesis," *Nature,* 2019; 566(7745):496-502.
Chen et al., "Single-cell whole-genome analyses by Linear Amplification via Transposon Insertion (LIANTI)," *Science,* 2017; 356:189-194.
Doležel, "Nuclear DNA Content and Genome Size of Trout and Human," *Cytometry Part A,* 2003; 51A:127-128.
Drmanac et al., "Human genome sequencing using unchained base reads on self- assembling DNA nanoarrays," *Science,* 2010; 327(5961):78-81.
Eberwine et al., "Analysis of gene expression in single live neurons," *Proceedings of the National Academy of Sciences,* 1992; 89:3010-3014.
Gabriel et al., "Linear Amplification mediated PCR—Localization of Genetic Elements and Characterization of Unknown Flanking DNA," *J Vis Exp,* 2014;88:e51543.
Hashimshony et al., "CEL-Seq: single-cell RNA-Seq by multiplexed linear amplification," *Cell Rep,* 2012; 2:666-673.
Lizardi et al., "Mutation detection and single-molecule counting using isothermal rolling-circle amplification," *Nature Genetics,* 1998; 19:225-232.
Mulqueen et al., "Highly scalable generation of DNA methylation profiles in single cells," *Nat. Biotechnol,* 2018; 36:428-431.
Ramani et al., "Massively multiplex single-cell Hi-C," *Nat. Methods,* 2017; 14:263-266.
Reuter et al., "Simul-seq: combined DNA and RNA sequencing for whole-genome and transcriptome profiling," *Nat Methods,* Nov. 2016; 13(11):953-958.
Sos et al., "Characterization of chromatin accessibility with a transposome hypersensitive sites sequencing (THS-seq) assay," *Genome Biol,* 2016; 17:20; 15 pages.
Yin et al., "High-throughput mapping of meiotic crossover and chromosome mis-segregation events in interspecific hyprid mice," *bioRxiv,* posted Jun. 4, 2018; 19 pages. Retrieved from the Internet: <URL:https://doi.org/10.1101/338053>.
Kirby et al., "Cryptic plasmids of *Mycobacterium avium:* Tn552 to the rescue," Mal. Microbial., Jan. 2002; 43 (1):173-86.
Kleckner et al., "Tnl0 and ISI0 transposition and chromosome rearrangements: mechanism and regulation in vivo and in vitro," Curr Top Microbial Immunol., 1996; 204:49-82.
Knouse et al., "Assessment of megabase-scale somatic copy numbervariation using single cell sequencing," Genome Res., Jan. 2016; doi: 10.1101/gr.198937.115.
Knouse et al., "Single cell sequencing reveals low levels of aneuploidy across mammalian tissues," Proc Natl Acad Sci USA, Sep. 2014; 11137:13409-13414.
Korlach, J. et al. "Selective aluminum passivation for targeted immobilization of single DNA polymerase molecules in zero-mode waveguide nanostructures." Proc. Natl. Acad Sci. USA, Jan. 2008; 1054:1176-1181.
Krishnaswami et al., Using Nuclei for RNA-Seq to Capture the Transcriptome of Postmortem Neurons, Nature Protocol, 2016, 113, 499-524. Year: 2016.
Kumagai et al., "Epigenetic regulation and molecular characterization of C/EBPalpha in pancreatic cancer cells," Int. J Cancer, Feb. 2009; 1244:827-833.
Kustatscher et al., Chromatin Enrichment for Proteomics, Nature Protocols, 2014, 99, 2090-2099. Year: 2014.
Lage et al., "Whole genome analysis of genetic alterations in small DNA samples using hyperbranched strand displacement amplification and array-CGH," Genome Res., Feb. 2003; 132:294-307.
Lampe et al., "A purified mariner transposase is sufficient to mediate transposition in vitro," The EMBO Journal, 1996; 1519:5470-9.
Langmead et al., "Fast gapped-read alignment with Bowtie 2," Nat Methods, Mar. 2012; 9:357-359.
Levene et al. "Zero-mode waveguides for single-molecule analysis at high concentrations," Science, Jan. 2003; 2995607:682-686.
Li et al., "DNA molecules and configurations in a solid-state nanopore microscope," Nature Materials, Aug. 2003; 2:611-615.
Lundquist et al. "Parallel confocal detection of single molecules in real time," Opt. Lett., May 2008; 339:1026-1028.
Macosko et al., "Highly Parallel Genome-wide Expression Profiling ofIndividual Cells Using Nanoliter Droplets," Cell, May 2015; 1615:1202-1214.
Masser et al., "Focused, high accuracy 5-methylcytosine quantitation with base resolution by benchtop next- generation sequencing," Epiginetics & Chromatin, 2013, vol. 6, No. 33, pp. 1-12.
McConnell et al., "Mosaic Copy Number Variation in Human Neurons," Science, Nov. 2013; 3426158:632-637.
Metzker, "Emerging technologies in DNA sequencing," Genome Res., Dec. 2005; 1512:1767-1776.
Mirkovitch et al., "Organization of the higher-order chromatin loop: specific DNA attachment sites on nuclear scaffold," Cell, Nov. 1984; 391:223-232.
Mizuuchi, "In vitro transposition of bacteriophage Mu: a biochemical approach to a novel replication reaction," Cell, Dec. 1983; 353 Pt 2:785-94.
Nagano et al., "Single-cell Hi-C reveals cell-to-cell variability in chromosome structure," Nature, Oct. 2013; 502:59-64.
Navin et al., "Tumour evolution inferred by single-cell sequencing," Nature, Apr. 2011; 472(7341):90-94.

(56) References Cited

OTHER PUBLICATIONS

Nextera, Nextera XT Library Prep: Tips and Troubleshooting, Illumina, 2015, 1-6. Year: 2015.
Nickerson et al., The Nuclear Matrix Revealed by Eluting Chromatin From a Cross-linked Nucleus, Proc. Natl. Acad. Sci., 1997, 94, 4446-4450. Year: 1997.
Ohtsubo et al., "Bacterial insertion sequences," Curr. Top. Microbial. Immunol., 1996; 204:1-26.
Olshen et al., "Circular binary segmentation for the analysis of array-based DNA copy number data," Biostatistics, Oct. 2004; 54:557-572.
Oyola et al., "Optimizing illumina next-generation sequencing library preparation for extremely at-biased genomes," BMC Genomics, 2012, vol. 13, No. 1, pp. 1-12.
Perkins, "Integrating cell-signalling pathways with NF-kappaB and IKK function," Nat. Rev. Mal. Cell Biol., Jan. 2007; 81:49-62.
Plasterk, "The Tel/mariner transposon family," Curr Topics Microbial. Immunol., 1996; 204:125-43.
Rehen et al., "Chromosomal variation in neurons of the developing and adult mammalian nervous system," Proc. Natl. Acad Sci. USA., Nov. 2001; 9823:13361-6.
Ronaghi et al., "A sequencing method based on real-time pyrophosphate," Science, Jul. 1998; 2815375:363, 365.
Ronaghi et al., "Real-time DNA sequencing using detection of pyrophosphate release," Analytical Biochemistry, Nov. 1996; 2421:84-9.
Ronaghi, "Pyrosequencing sheds light on DNA sequencing," Genome Res., Jan. 2001; 11(1):3-11.
Rosenkrantz et al., "Investigating somatic aneuploidy in the brain: why we need a new model," Chromosoma, Jun. 2017; 1263:337-350.
Ruparel et al., "Design and synthesis of a 3'-O-allyl photocleavable fluorescent nucleotide as a reversible terminator for DNA sequencing by synthesis," Proc. Natl. Acad Sci. USA, Apr. 2005; 10217:5932-7.
Savilahti et al., "The phage Mu transpososome core: DNA requirements for assembly and function," EMBO J, Oct. 1995; 1419:4893-4903.
Shalek, Baring cellular souls, Science Translational Medicine, Feb. 15, 2017, vol. 9, Issue 377.
Sigma-Aldrich, "Detergents and Solubilization Reagents," Biofiles for Life Science Research, 2008, vol. 3, No. 3, pp. 1-36.
Soni et al., "Progress toward ultrafast DNA sequencing using solid-state nanopores," Clin. Chem., Nov. 2007; 5311:1996-2001.
Stahley et al., "Desmosomes in acquired disease," Cell Tissue Res., Jun. 2015; 3603:439-56.
Stergachis et al., "Developmental fate and cellular maturity encoded in human regulatory DNA landscapes," Cell, Aug. 2013; 1544:888-903.
The ENCODE Project Consortium, "An integrated encyclopedia of DNA elements in the human genome," Nature, Sep. 2012; 4897414:57-74.
Tomschik et al., "Fast, long-range, reversible conformational fluctuations in nucleosomes revealed by single-pair fluorescence resonance energy transfer," Proc. Natl. Acad Sci. USA., Mar. 1, 2005; 1029:3278-3283.
Vitak et al., "Construction of thousands of single cell genome sequencing libraries using combinatorial indexing," bioRxiv, 2016, 18 pages.
Vitak et al., "SCI-seq: Sequencing thousands of single-cell genomes with combinatorial indexing," Nature Methods, doi:10.1038/nmeth.4154; 41 pages.
Waddell et al., "Whole genomes redefine the mutational landscape of pancreatic cancer," Nature, Feb. 2015; 5187540:495-501.
Walker et al., "Strand displacement amplification—an isothermal, in vitro DNA amplification technique," Nucl. Acids Res., Apr. 1992; 207:1691-96.
White et al., The Impact of Detergents on the Tissue Decellularization Process: A ToF-SIMS Study, Acta Biomaterialia, 2017, 50, 207-219. Year: 2017.
Wilson et al., "New transposon delivery plasmids for insertional mutagenesis in Bacillus anthracis," J Microbial. Methods, Dec. 2007; 713:332-5.
Wilson et al., Improved Immunodetection of Nuclear Antigens After Sodium Dodecyl Sulfate Treatment of Formaldehyde-Fixed Cells, Journal of Histochemistry & Cytochemistry, 1999, 478, 1095-1100. Year: 1999.
Adey et al., "In vitro, long-range sequence information for de novo genome assembly via transposase contiguity," Genome Res., Oct. 2014; 24:2041-2049.
Adey et al., "Rapid, low-input, low-bias construction of shotgun fragment libraries by high-density in vitro transposition," Genome Biol., 2010; 11:R1 19, 1-17.
Adey et al., "The haplotype-resolved genome and epigenome of the aneuploid HeLa cancer cell line," Nature, Aug. 2013; 5007461:207-211.
Alberts et al., Molecular Biology of the Cell, 4th ed., New York: Garland Science; 2002. Available online at <ncbi.nlm.nih.gov/books/NBK26834/#630>, obtained on Oct. 10, 2019; excerpt from section title "Nucleosomes Are the Basic Unit of Eucaryotic Chromosome Structure". 1 pg.
Arrigoni et al., Standardizing Chromatin Research: A Simple and Universal Method for ChIP-Seq, Nucleic Acids Reasearch, 2015, 44(7), 1-13. (Year: 2015).
Bailey et al., "Genomic analyses identify molecular subtypes of pancreatic cancer," Nature, Mar. 2016; 531 (7592):47-52.
Baslan et al., "Optimizing sparse sequencing of single cells for highly multiplex copy number profiling," Genome Res., Apr. 2015; 25:714-724.
Beitel et al., "Strain- and plasmid-level deconvolution of a synthetic metagenome by sequencing proximity ligation products," PeerJ, May 2014; 2:e415.
Bentley et al., "Accurate whole genome sequencing using reversible terminator chemistry," Nature, Nov. 2008; 456(7218):53-59.
Boeke et al., "Transcription and reverse transcription of retrotransposons," Annu Rev Microbial., 1989; 43:403-34.
Borrell et al., The Action of Triton X-100 and Sodium Dodecyl Sulphate on Lipid Layers. Effect on Monolayers and Liposomes, Journal of Microencapsulation, 1990, 7(2), 255-259 (Year: 1990).
Brown et al., "Retroviral integration: structure of the initial covalent product and its precursor, and a role for the viral IN protein," Proc Natl Acad Sci USA, Apr. 1989; 86(8):2525-9.
Buenrostro et al., Transposition of Native Chromatin for Fast and Sensitive Epigenomic Profiling of Open Chromatin, DNA-Binding Proteins and Nucelosome Position, Nature Methods, 2013, 10(12), 1213-1218. (Year: 2013).
Burton et al., "Species-level deconvolution of metagenome assemblies with Hi-C-based contact probability maps," G3 (Bethesda). May 2014; 4(7):1339-46.
Cai et al. "Single-Cell, Genome-wide Sequencing Identifies Clonal Somatic Copy-Number Variation in the Human Brain," Cell Rep., Sep. 2014; 8:1280-1289.
Callaway, "'Platinum' genome takes on disease," Nat. News, Nov. 2014; 515(7527):323.
Clyde, "Barcoding the nucleus", Nature Reviews Genetics, published online Feb. 13, 2017, doi:10.1038/nrg.2017.11.
Cockroft et al., "A single-molecule nanopore device detects DNA polymerase activity with single-nucleotide resolution," J Am. Chem. Soc., Jan. 2008; 130(3):818-820.
Colegio et al., "In vitro transposition system for efficient generation of random mutants of Campylobacterjejuni," J Bacterial., Apr. 2001; 183(7):2384-8.
Craig, "Transposon Tn7," Curr Top Microbial. Immunol., 1996; 204:27-48.
Craig, "V(D)J recombination and transposition: closer than expected," Science, Mar. 1996; 271(5255):1512.
Cusanovich et al., Supplementary Materials, Multiplex Single-Cell Profiling of Chromatin Accessibility by Combinatorial Cellular Indexing, Science, 2015, 1-34. (Year: 2015).
De Kouchkovsky et al., "Acute myeloid leukemia: a comprehensive review and 2016 update," Blood Cancer J, Jul. 2016; 6(7):e441.
Deamer et al., "Characterization of nucleic acids by nanopore analysis," Acc. Chem. Res., Oct. 2002; 35 (10):817-825.

(56) References Cited

OTHER PUBLICATIONS

Deamer et al., "Nanopores and nucleic acids: prospects for ultrapid sequencing," Trends Biotechnol., Apr. 2000; 18 (4):147-151.
Dean et al., "Comprehensive human genome amplification using multiple displacement amplification," Proc. Natl. Acad Sci. USA, Apr. 2002; 99(8):5261-66.
Devine et al., "Efficient integration of artificial transposons into plasmid targets in vitro: a useful tool for DNA mapping, sequencing and genetic analysis," Nucleic Acids Res., Sep. 1994; 22(18):3765-72.
Eirew et al., "Dynamics of genomic clones in breast cancer patient xenografts at single-cell resolution," Nature, Feb. 2015; 518:422-6.
Forbes et al. "COSMIC: Exploring the world's knowledge of somatic mutations in human cancer," Nucleic Acids Res., Jan. 2015; 43:D805-D811.
Gao et al., "Punctuated copy number evolution and clonal stasis in triple-negative breast cancer," Nat. Genet., October 2016; 48(10):1119-1130.
Garvin et al., "Interactive analysis and quality assessment of single-cell copy-number variations," bioRxiv, November 2014; 1-32. doi:10.1101/011346.
Gawad et al., "Dissecting the clonal origins of childhood acute lymphoblastic leukemia by single-cell genomics," Proc. Natl. Acad Sci. USA., Dec. 2014; 111(50):17947-52.
Gawad et al., "Single-cell genome sequencing: current state of the science," Nat. Rev. Genet., Jan. 2016; 17:175-88.
Gloor, "Gene targeting in *Drosophila,*" Methods Mal. Biol., 2004; 260:97-114.
Goldenberger et al., A Simple "Universal" DNA Extraction Procedure Using SDS and Proteinase K Is Compatible with Direct PCR Amplification, PCR Methods and Applications, 1995, 4, 368-370. (Year: 1995).
Goryshin et al., "Tn5 in vitro transposition," J Biol. Chem., Mar. 1998; 273(13):7367-74.
Goryshin et al., "Tn5/IS50 target recognition," Proc. Natl. Acad Sci. USA, Sep. 1998; 95(18)10716-10721.
Gravina et al., "Single-cell, locus-specific bisulfite sequencing (SLBS) for direct detection of epimutations in DNA methylation patterns," Nucleic Acids Research, 2015, vol. 43, No. 14, e93, pp. 1-7.
Ha et al., "Integrative analysis of genome-wide loss of heterozygosity and monoallelic expression at nucleotide resolution reveals disrupted pathways in triple-negative breast cancer," Genome Research, Oct. 2012; 22 (10):1995-2007.
Healy, "Nanopore-based single-molecule DNA analysis," Nanomedicine (Land)., Aug. 2007; 2( 4):459-481.
Hoffman et al., "Formaldehyde Crosslinking: A Tool for the Study of Chomatin Complexes," J Biol. Chem., Oct. 2015; 290(44):26404-26411.
Ichikawa, "In vitro transposition of transposon Tn3," J Biol. Chem., Nov. 1990; 265(31):18829-32.
Illumina® Safety Data Sheet, LP#-TSB, Tagment Stop Buffer, Issued Nov. 12, 2018, Revised Jan. 22, 2020, Revision No. 4.2.
Illumina® Safety Data Sheet, NX#-TD, Tagment DNA Buffer, Issued Jun. 5, 2018, Revised Jan. 22, 2020, Revision No. 2.4.
Illumina® Safety Data Sheet, NX#-TDE1 Tagment DNA Enzyme 1, Issued Jan. 15, 2018, Revised Jan. 22, 2020, Revision No. 1.1.
International Preliminary Report on Patentability in PCT/US2017/043381, mailed Jan. 22, 2019, 8 pages.
International Preliminary Report on Patentability in PCT/US2018/036078, mailed Dec. 10, 2019, 7 pages.
International Search Report and Written Opinion for International Application No. PCT/US2017/043381, dated Nov. 15, 2017, 17 pages.
Jackson et al., "Evaluating bias-reducing protocols for RNA sequencing library preparation," BMC Genomics, 2014, vol. 15, No. 569, pp. 1-9.
Kawashima et al., Efficient Extraction of Proteins From Formalin-Fixed Paraffin-Embedded Tissues Requires Higher Concentration of Tris(hydroxymethyl)aminomethane, Clinical Proteomics, 2014, 11(4), 1-6. (Year: 2014).
Zhang et al., "A Novel Mechanism of Transposon-Mediated Gene Activation," PLoS Genet., Oct. 2009; 5(10): el000689.
Zilionis et al., "Single-cell barcoding and sequencing using droplet microfluidics," Nature Protocols, 2017, vol. 12, No. 1, pp. 44-73.
Zong et al., "Genome-Wide Detection of Single Nucleotide and Copy Number Variations of a Single Human Cell," Science, 2012; 338(6114): 1622-1626.
Ohmori et al., "Detection of 5-methylcytosine in DNA sequences," May 5, 1978, *Nucleic Acid Res.,* 5(5):1479-86.
Zadesenets et al., "Whole-Genome Sequencing of Eukaryotes: From Sequencing of DNA Fragments to a Genome Assembly," 2017, *Russian Journal of Genetics,* 53(6): 641-50.
Buenrostro J.D., et al., "Single-cell Chromatin Accessibility Reveals Principles of Regulatory Variation", Nature, Jul. 23, 2025, vol. 523, No. 7561, pp. 486-490 (20 Pages).
Miura F., et al., "Amplification-Free Whole-Genome Bisulfite Sequencing by Post-bisulfite Adaptor Tagging", Nucleic Acids Research, 2012, vol. 40, No. 17, e136-e136, pp. 1-9.
Caruccio N., "Preparation of Next-generation Sequencing Libraries Using Nextera Technology: Simultaneous DNA Fragmentation and Adaptor Tagging by in Vitro Transposition", Methods in Molecular Biology, 2011, vol. 733, pp. 241-255.
Illumina: "Illumina Sequencing Technology", Technology Spotlight: Illumina Sequencing, 2010, 5 Pages.
Kaper F., et al., "Whole-Genome Haplotyping by Dilution, Amplification, and Sequencing", PNAS, Apr. 2, 2013, vol. 110, No. 14, pp. 5552-5557.
Marine R., et al., "Evaluation of a Transposase Protocol for Rapid Generation of Shotgun High-throughput Sequencing Libraries from Nanogram Quantities of DNA", Applied and Environmental Microbiology, Nov. 2011, vol. 77, No. 22, pp. 8071-8079.
Rio D.C., et al., "Purification of RNA by SDS Solubilization and Phenol Extraction", Cold Spring Harbor Protocol, Jun. 2010, vol. 2010, No. 6, pp. 1-5.
Vaidyanathan S., et al., "Detergent Induction of HEK293A Cell Membrane Permeability Measured Under Quiescent and Superfusion Conditions Using Whole Cell Patch Clamp", The Journal of Physical Chemistry, Feb. 27, 2014, vol. 118, No. 8, pp. 2112-2123.

* cited by examiner

SINGLE CELL WHOLE GENOME LIBRARIES FOR METHYLATION SEQUENCING

CROSS-REFERENCE TO RELATED APPLICATIONS

This application claims the benefit of U.S. Provisional Application Ser. No. 62/516,324, filed Jun. 7, 2017, which is incorporated by reference herein.

GOVERNMENT FUNDING

This invention was made with government support under R35 GM124704 awarded by National Institutes of Health. The government has certain rights in the invention.

SEQUENCE LISTING

This application contains a Sequence Listing electronically submitted via Patent Center to the United States Patent and Trademark Office as an ASCII text file entitled "0531.001584US01_seqlist_ST25.txt" having a size of 28,672 bytes and created on Apr. 17, 2026. The information contained in the Sequence Listing is incorporated by reference herein.

FIELD

Embodiments of the present disclosure relate to sequencing nucleic acids. In particular, embodiments of the methods and compositions provided herein relate to producing single-cell bisulfite sequencing libraries and obtaining sequence data therefrom.

BACKGROUND

High cell count single-cell sequencing has shown its efficacy in separation of populations within complex tissues via transcriptomes, chromatin-accessibility, and mutational differences. Further, single-cell resolution has allowed for cell differentiation trajectories to be assessed at genomic-specific patterns, such as methylation of DNA. DNA methylation is a covalent addition to cytosine; a mark with cell type-specificity that is the subject of active modification in developing tissues. DNA methylation can be probed at base pair resolution using the deaminating chemistry of sodium bisulfite treatment.

Recent work has optimized bisulfite sequencing so far as to require single-cell inputs in either single cell reduced representation bisulfite sequencing (scRRBS) or single cell whole genome bisulfite sequencing (scWGBS). However, these methods lack scalability, relying on single-cell deconvolution via parallel and isolated library generation in which single cell reactions are performed in isolation. An entirely new set of reagents is required for each cell sequencing, resulting in linear scaling of costs for each additional cell. Due to the challenges of bisulfite conversion of DNA, no droplet- or chip-based microfluidics systems have been deployed for single cell bisulfite sequencing, nor do any theoretically-viable strategies exist using alternative platforms.

SUMMARY OF THE APPLICATION

Provided herein are compositions and scaleable high-cell count, single-cell methylome profiling assays. Single-cell whole genome sequencing (scWGBS) is improved by the single-cell combinatorial indexing strategies provided herein, such that cells can be processed in bulk, and single-cell output demultiplexed in silico. In some embodiments, the methods provided herein make use of transposase-based adaptor incorporation which results in increased efficiency and much higher alignment rates over existing methods. The use of transposase to append one of the two sequencing adaptors enables much more efficient library construction with fewer noise reads, thus resulting in an alignment rate of ~60% (similar rates as bulk cell strategies) when compared to 10-30% using single-cell-single-well methods. This results in more useable sequence reads and a dramatic cost reduction for the sequencing portion of the assay. The use of single-cell combinatorial indexing strategies to produce single-cell bisulfite sequencing libraries is demonstrated on a mix of human and mouse cells with a minimal collision rate. Also demonstrated is the successful deconvolution of a mix of three human cell types and achieve a cell type assignment using publicly available data.

Definitions

As used herein, the terms "organism," "subject," are used interchangeably and refer to animals and plants. An example of an animal is a mammal, such as a human.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to urinary bladder, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, ovary epithelial, ovary fibroblast, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver Alexander, liver fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial, and stomach fibroblast.

As used herein, the term "tissue" is intended to mean a collection or aggregation of cells that act together to perform one or more specific functions in an organism. The cells can optionally be morphologically similar. Exemplary tissues include, but are not limited to, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of a human or other organism. A tissue can be a healthy tissue or an unhealthy tissue. Examples of unhealthy tissues include, but are not limited to, a variety of malignancies with aberrant methylation, for example, malignancies in lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinomas, adenocarcinomas, sarcomas, fibroadenocarcinoma, neuroendocrine, or undifferentiated.

As used herein, the term "compartment" is intended to mean an area or volume that separates or isolates something from other things. Exemplary compartments include, but are not limited to, vials, tubes, wells, droplets, boluses, beads, vessels, surface features, or areas or volumes separated by physical forces such as fluid flow, magnetism, electrical current or the like. In one embodiment, a compartment is a well of a multi-well plate, such as a 96- or 384-well plate.

As used herein, a "transposome complex" refers to an integration enzyme and a nucleic acid including an integration recognition site. A "transposome complex" is a functional complex formed by a transposase and a transposase recognition site that is capable of catalyzing a transposition reaction (see, for instance, Gunderson et al., WO 2016/130704). Examples of integration enzymes include, but are not limited to, such as an integrase or a transposase. Examples of integration recognition sites include, but are not limited to, a transposase recognition site.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. Examples of non-native bases include a locked nucleic acid (LNA) and a bridged nucleic acid (BNA). LNA and BNA bases can be incorporated into a DNA oligonucleotide and increase oligonucleotide hybridization strength and specificity. LNA and BNA bases and the uses of such bases are known to the person skilled in the art and are routine.

As used herein, the term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample, such as a nucleus. In one embodiment, the targets can be processed into templates suitable for amplification by the placement of universal sequences at the ends of each target fragment. The targets can also be obtained from a primary RNA sample by reverse transcription into cDNA.

As used herein, the term "universal," when used to describe a nucleotide sequence, refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids, e.g., capture oligonucleotides, that are complementary to a portion of the universal sequence, e.g., a universal capture sequence. Non-limiting examples of universal capture sequences include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal anchor sequence. A capture oligonucleotide or a universal primer therefore includes a sequence that can hybridize specifically to a universal sequence.

The terms "P5" and "P7" may be used when referring to amplification primers, e.g., a capture oligonucleotide. The terms "P5'" (P5 prime) and "P7'" (P7 prime) refer to the complement of P5 and P7, respectively. It will be understood that any suitable amplification primers can be used in the methods presented herein, and that the use of P5 and P7 are exemplary embodiments only. Uses of amplification primers such as P5 and P7 on flowcells are known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture and/or amplification of nucleic acids as presented herein.

As used herein, the term "primer" and its derivatives refer generally to any nucleic acid that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the term "adapter" and its derivatives, e.g., universal adapter, refers generally to any linear oligonucleotide which can be ligated to a nucleic acid molecule of the disclosure. In some embodiments, the adapter is substantially non-complementary to the 3' end or the 5' end of any target sequence present in the sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream error correction, identification or sequencing. The terms "adaptor" and "adapter" are used interchangeably.

As used herein, the term "each," when used in reference to a collection of items, is intended to identify an individual item in the collection but does not necessarily refer to every item in the collection unless the context clearly dictates otherwise.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ and can also include various modifiers of ionic strength.

As used herein, "re-amplification" and their derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the re-amplification can involve the use of different amplification conditions and/or different primers, including different target-specific primers than the primary amplification.

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of $^{32}$P-labeled deoxynucleotide triphosphates into the amplified target sequence).

As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

BRIEF DESCRIPTION OF THE FIGURES

The following detailed description of illustrative embodiments of the present disclosure may be best understood when read in conjunction with the following drawings.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION OF ILLUSTRATIVE EMBODIMENTS

Figure 1:
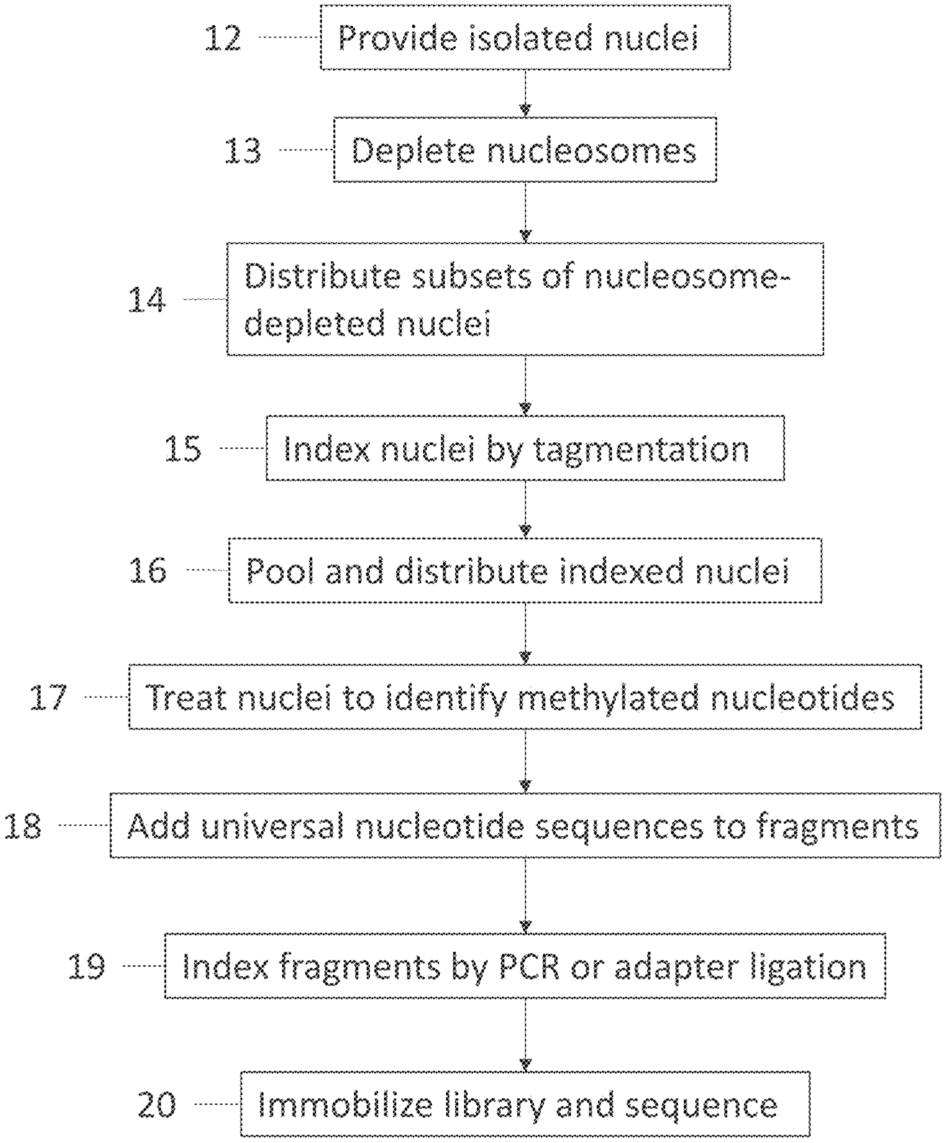
FIG. 1 shows a general block diagram of a general illustrative method for single-cell combinatorial indexing according to the present disclosure.
Figure 2A:
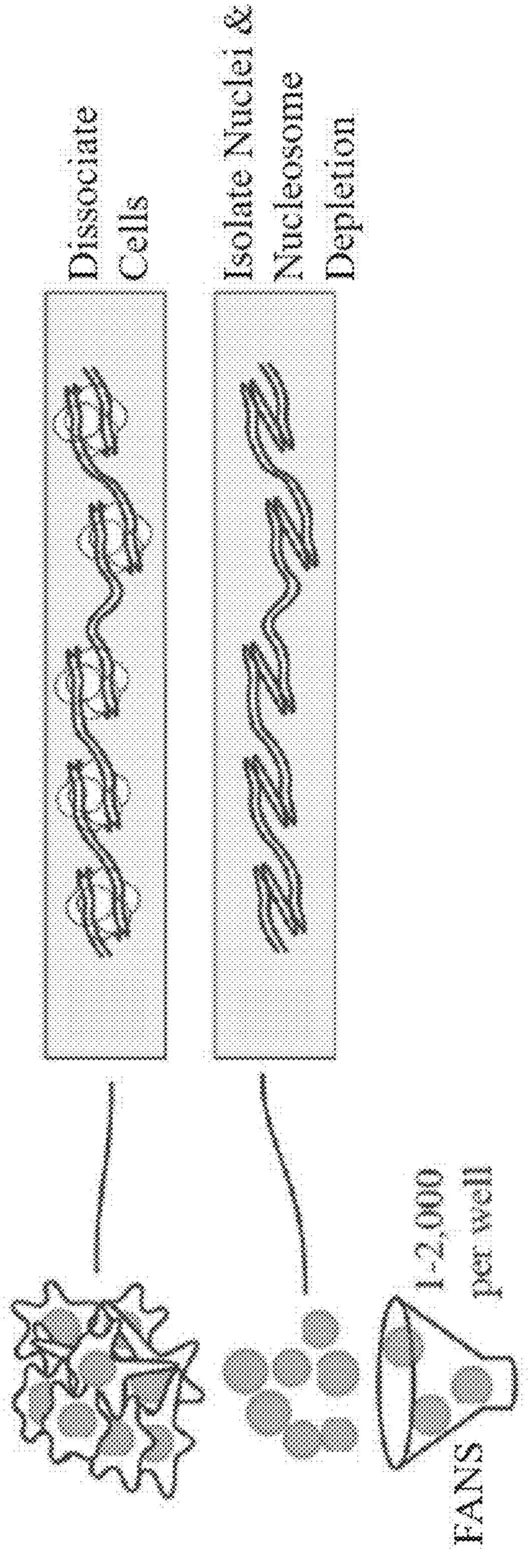
FIG. 2A-FIG. 2D shows a schematic drawing of one embodiment of the method for single-cell combinatorial indexing generally illustrated in FIG. 1.
Figure 2B:
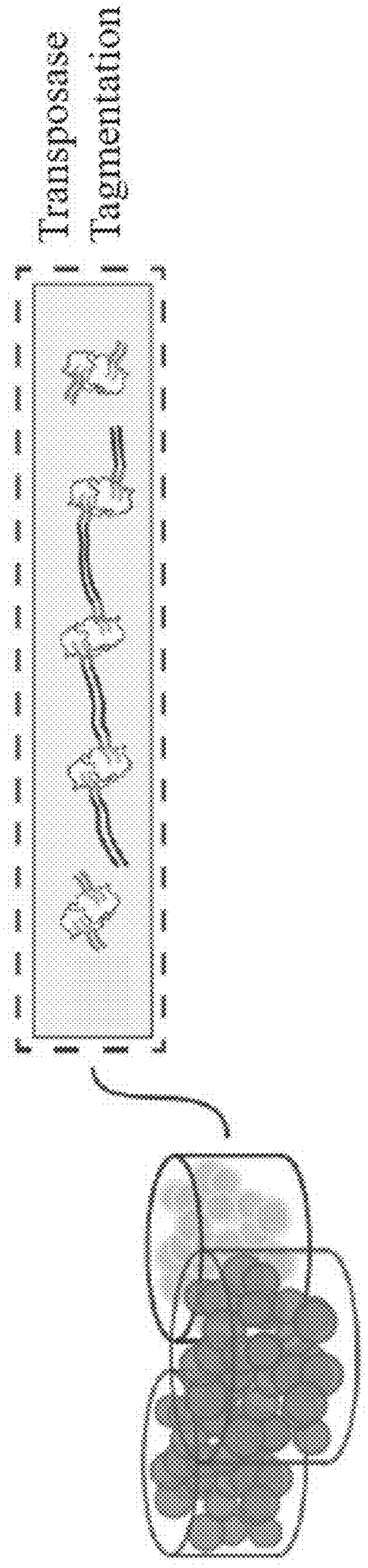
Figure 2C:
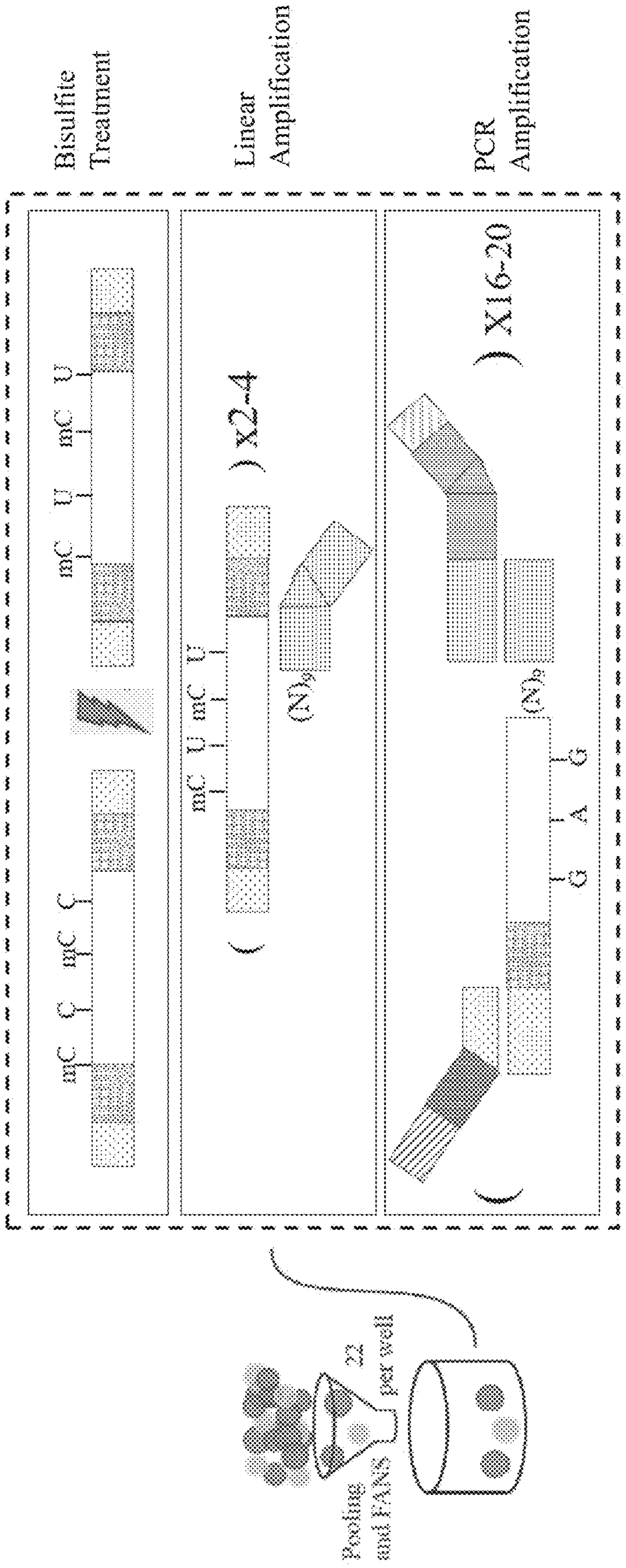
Figure 2D:
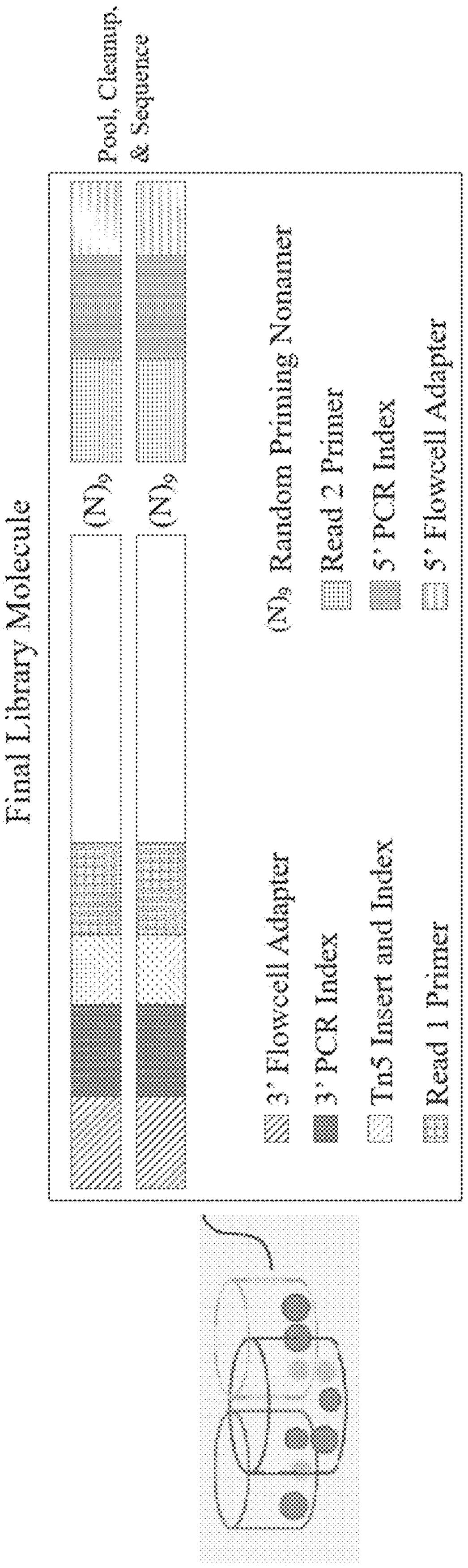

The method provided herein includes providing isolated nuclei from a plurality of cells (FIG. 1, block 12). The cells can be from any organism(s), and from any cell type or any tissue of the organism(s). The method can further include dissociating cells (FIG. 2, block i), and/or isolating the nuclei (FIG. 2, block ii). Methods for isolating nuclei from cells are known to the person skilled in the art and are routine. The number of nuclei can be at least 2. The upper limit is dependent on the practical limitations of equipment (e.g. multi-well plates) used in other steps of the method as described herein. For instance, in one embodiment the number of nuclei can be no greater than 1,000,000,000, no greater than 100,000,000, no greater than 10,000,000, no greater than 1,000,000, no greater than 10,000, or no greater than 1,000. The skilled person will recognize that the nuclei acid molecules in each nucleus represent the entire genetic complement of an organism, and are genomic DNA molecules which include both intron and exon sequences, as well as non-coding regulatory sequences such as promoter and enhancer sequences.

In one embodiment, the nuclei include nucleosomes bound to genomic DNA. Such nuclei can be useful in methods that do not determine the DNA sequence of the whole genome of a cell, such as sciATAC-seq. In another embodiment, the isolated nuclei are subjected to conditions that deplete the nuclei of nucleosomes, generating nucleosome-depleted nuclei (FIG. 1, block 13, and FIG. 2, block ii). Such nuclei can be useful in methods aimed at determining the whole genomic DNA sequence of a cell. In one embodiment, the conditions used for nucleosome-depletion maintain the integrity of the isolated nuclei. Methods for generating nucleosome depleted nuclei are known to the skilled person (see, for instance, Vitak et al., 2017, Nature Methods, 14 (3): 302-308). In one embodiment, the conditions are a chemical treatment that includes a treatment with a chaotropic agent capable of disrupting nucleic acid-protein interactions. An example of a useful chaotropic agent includes, but is not limited to, lithium diiodosalicylate. In another embodiment, the conditions are a chemical treatment that includes a treatment with a detergent capable of disrupting nucleic acid-protein interactions. An example of a useful detergent includes, but is not limited to, sodium dodecyl sulfate (SDS). In some embodiments, when a detergent such as SDS is used, the cells from which the nuclei are isolated are treated with a cross-linking agent prior to the isolating. A useful example of a cross-linking agent includes, but is not limited to, formaldehyde.

The method provided herein includes distributing subsets of the nuclei, such as nucleosome-depleted nuclei, into a first plurality of compartments (FIG. 1, block 14, and FIG. 2, left schematic). The number of nuclei present in a subset, and therefor in each compartment, can be at least 1. In one embodiment, the number of nuclei present in a subset is no greater than 2,000. Methods for distributing nuclei into subsets are known to the person skilled in the art and are routine. Examples include, but are not limited to, fluorescence-activated nuclei sorting (FANS).

Each compartment includes a transposome complex. The transposome complex, a transposase bound to a transposase recognition site, can insert the transposase recognition site into a target nucleic acid within a nucleus in a process sometimes termed "tagmentation." In some such insertion events, one strand of the transposase recognition site may be transferred into the target nucleic acid. Such a strand is referred to as a "transferred strand." In one embodiment, a transposome complex includes a dimeric transposase having two subunits, and two non-contiguous transposon sequences. In another embodiment, a transposase includes a dimeric transposase having two subunits, and a contiguous transposon sequence.

Some embodiments can include the use of a hyperactive Tn5 transposase and a Tn5-type transposase recognition site (Goryshin and Reznikoff, *J. Biol. Chem.,* 273:7367 (1998)), or MuA transposase and a Mu transposase recognition site comprising R1 and R2 end sequences (Mizuuchi, K., *Cell,* 35:785, 1983; Savilahti, H, et al., *EMBO J.,* 14:4893, 1995). Tn5 Mosaic End (ME) sequences can also be used as optimized by a skilled artisan.

More examples of transposition systems that can be used with certain embodiments of the compositions and methods provided herein include *Staphylococcus aureus* Tn552 (Colegio et al., *J. Bacteriol.,* 183:2384-8, 2001; Kirby C et al., *Mol. Microbiol.,* 43:173-86, 2002), Ty1 (Devine & Boeke, *Nucleic Acids Res.,* 22:3765-72, 1994 and International Publication WO 95/23875), Transposon Tn7 (Craig, NL, *Science.* 271:1512, 1996; Craig, NL, Review in: *Curr Top Microbiol Immunol.,* 204:27-48, 1996), Tn/O and IS10 (Kleckner N, et al., *Curr Top Microbiol Immunol.,* 204:49-82, 1996), Mariner transposase (Lampe D J, et al., *EMBO J.,* 15:5470-9, 1996), Tcl (Plasterk R H, *Curr. Topics Microbiol. Immunol.,* 204:125-43, 1996), P Element (Gloor, G B, *Methods Mol. Biol.,* 260:97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204:1-26, 1996), retroviruses (Brown, et al., *Proc Natl Acad Sci USA,* 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLOS Genet.* 5: e1000689. Epub 2009 Oct. 16; Wilson C. et al (2007) *J. Microbiol. Methods* 71:332-5).

Other examples of integrases that may be used with the methods and compositions provided herein include retroviral integrases and integrase recognition sequences for such retroviral integrases, such as integrases from HIV-1, HIV-2, SIV, PFV-1, RSV.

Transposon sequences useful with the methods and compositions described herein are provided in U.S. Patent Application Pub. No. 2012/0208705, U.S. Patent Application Pub. No. 2012/0208724 and Int. Patent Application Pub. No. WO 2012/061832. In some embodiments, a transposon sequence includes a first transposase recognition site, a second transposase recognition site, and an index present between the two transposase recognition sites.

Some transposome complexes useful herein include a transposase having two transposon sequences. In some such embodiments, the two transposon sequences are not linked to one another, in other words, the transposon sequences are non-contiguous with one another. Examples of such transposomes are known in the art (see, for instance, U.S. Patent Application Pub. No. 2010/0120098).

In some embodiments, a transposome complex includes a transposon sequence nucleic acid that binds two transposase subunits to form a "looped complex" or a "looped transposome." In one example, a transposome includes a dimeric transposase and a transposon sequence. Looped complexes can ensure that transposons are inserted into target DNA while maintaining ordering information of the original target DNA and without fragmenting the target DNA. As will be appreciated, looped structures may insert desired nucleic acid sequences, such as indexes, into a target nucleic acid, while maintaining physical connectivity of the target nucleic acid. In some embodiments, the transposon sequence of a looped transposome complex can include a fragmentation site such that the transposon sequence can be fragmented to create a transposome complex comprising two transposon sequences. Such transposome complexes are useful to ensuring that neighboring target DNA fragments, in which the transposons insert, receive code combinations that can be unambiguously assembled at a later stage of the assay.

A transposome complex also includes at least one index sequence, also referred to as a transposase index. The index sequence is present as part of the transposon sequence. In one embodiment, the index sequence can be present on a transferred strand, the strand of the transposase recognition site that is transferred into the target nucleic acid. An index sequence, also referred to as a tag or barcode, is useful as a marker characteristic of the compartment in which a particular target nucleic acid was present. The index sequence of a transposome complex is different for each compartment. Accordingly, in this embodiment, an index is a nucleic acid sequence tag which is attached to each of the target nucleic acids present in a particular compartment, the presence of which is indicative of, or is used to identify, the compartment in which a population of nuclei were present at this stage of the method.

An index sequence can be up to 20 nucleotides in length, e.g., 1, 2, 3, 4, 5, 6, 7, 8, 9, 10, 11, 12, 13, 14, 15, 16, 17, 18, 19, 20. A four nucleotide tag gives a possibility of multiplexing 256 samples on the same array, a six base tag enables 4096 samples to be processed on the same array.

In one embodiment, the transferred strand can also include a universal sequence, a first sequencing primer sequence, or a combination thereof. Universal sequences and sequencing primer sequences are described herein. Thus, in some embodiments where the transferred strand is transferred to target nucleic acids, the target nucleic acids include a transposase index, and also include a universal sequence, a first sequencing primer sequence, or a combination thereof.

In one embodiment, the cytosine nucleotides of a transferred strand are methylated. In another embodiment, the nucleotides of a transferred strand do not contain cytosine. Such a transferred strand, and any sequence present on the transferred strand including a transposase index sequence, universal sequence, and/or first sequencing primer sequence, can be referred to as cytosine-depleted. The use of cytosine-depleted nucleotide sequences in a transposome complex does not have a significant impact on transposase efficiency.

The method also includes generating indexed nuclei (FIG. 1, block 15, and FIG. 2, block iii). In one embodiment, generating indexed nuclei includes fragmenting nucleic acids present in the subsets of nucleosome-depleted nuclei (e.g., the nuclei acids present in each compartment) into a plurality of nucleic acid fragments. In one embodiment, fragmenting nucleic acids is accomplished by using a fragmentation site present in the nucleic acids. Typically, fragmentation sites are introduced into target nucleic acids by using a transposome complex. For instance, a looped transposome complex can include a fragmentation site. A fragmentation site can be used to cleave the physical, but not the informational association between index sequences that have been inserted into a target nucleic acid. Cleavage may be by biochemical, chemical or other means. In some embodiments, a fragmentation site can include a nucleotide or nucleotide sequence that may be fragmented by various means. Examples of fragmentation sites include, but are not limited to, a restriction endonuclease site, at least one ribonucleotide cleavable with an RNAse, nucleotide analogues cleavable in the presence of certain chemical agent, a diol linkage cleavable by treatment with periodate, a disulfide group cleavable with a chemical reducing agent, a cleavable moiety that may be subject to photochemical cleavage, and a peptide cleavable by a peptidase enzyme or other suitable means (see, for instance, U.S. Patent Application Pub. No. 2012/0208705, U.S. Patent Application Pub. No. 2012/0208724 and WO 2012/061832. The result of the fragmenting is a population of indexed nuclei, each nucleus containing nucleic acid fragments, where the nucleic acid fragments include on at least one strand the index sequence indicative of the particular compartment.

The indexed nuclei from multiple compartments can be combined (FIG. 1, block 16, and FIG. 2, schematic on left). For instance, the indexed nuclei from 2 to 96 compartments (when a 96-well plate is used), or from 2 to 384 compartments (when a 384-well plate is used) are combined. Subsets of these combined indexed nuclei, referred to herein as pooled indexed nuclei, are then distributed into a second plurality of compartments. The number of nuclei present in a subset, and therefor in each compartment, is based in part on the desire to reduce index collisions, which is the presence of two nuclei having the same transposase index ending up in the same compartment in this step of the method. The number of nuclei present in a subset in this embodiment can be from 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30. In one embodiment, the number of nuclei present in a subset is from 20 to 24, such as 22. Methods for distributing nuclei into subsets are known to the person skilled in the art and are routine. Examples include, but are not limited to, fluorescence-activated nuclei sorting (FANS).

The distributed indexed nuclei are treated to identify methylated nucleotides (FIG. 1, block 17, and FIG. 2, block iv). Methylation of sites, such as CpG dinucleotide sequences, can be measured using any of a variety of techniques used in the art for the analysis of such sites. One useful method is the identification of methylated CpG dinucleotide sequences. The identification of methylated CpG dinucleotide sequences is determined using cytosine conversion based technologies, which rely on methylation status-dependent chemical modification of CpG sequences within isolated genomic DNA, or fragments thereof, followed by DNA sequence analysis. Chemical reagents that are able to distinguish between methylated and non-methylated CpG dinucleotide sequences include hydrazine, which cleaves the nucleic acid, and bisulfite. Bisulfite treatment followed by alkaline hydrolysis specifically converts non-methylated cytosine to uracil, leaving 5-methylcytosine unmodified as described by Olek A., 1996, *Nucleic Acids Res.* 24:5064-6 or Frommer et al., 1992, *Proc. Natl. Acad. Sci. USA* 89:1827-1831. The bisulfite-treated DNA can subsequently be analyzed by molecular techniques, such as PCR amplification, sequencing, and detection including oligonucleotide hybridization (e.g. using nucleic acid microarrays). In one embodiment, the indexed nuclei in each compartment are exposed to conditions for bisulfite treatment. Bisulfite treatment of nucleic acids is known to the person skilled in the art and is routine. In one embodiment, the bisulfite treatment converts unmethylated cytosine residues of CpG dinucleotides to uracil residues and leaves 5-methylcytosine residues unaltered. Bisulfite treatment results in bisulfite-treated nucleic acid fragments.

Figure 3:
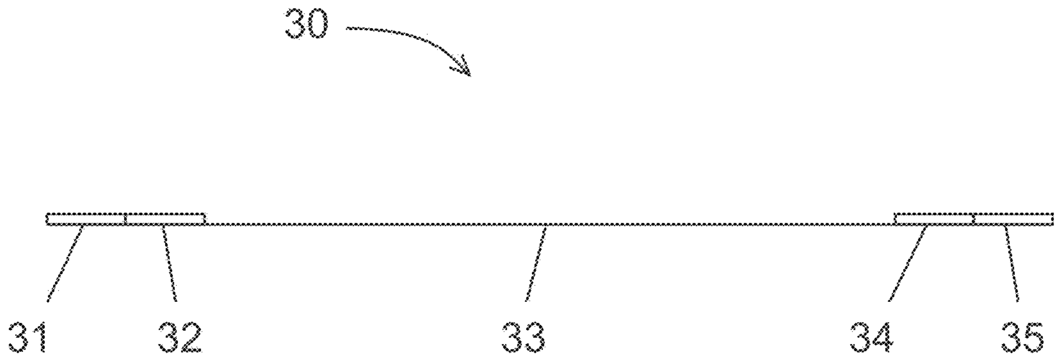
FIG. 3 shows a schematic drawing of an illustrative embodiment of a fragment-adapter molecule after linear amplification.

After generation of the bisulfite-treated nucleic acid fragments, the fragments are modified to include additional nucleotides at one or both ends (FIG. 1, block 18, and FIG. 2, blocks v and vi). In one embodiment, the modification includes subjecting the bisulfite-treated nucleic acid fragments to linear amplification using a plurality of primers. Each primer includes at least two regions; a universal nucleotide sequence at the 5' end and a random nucleotide sequence at the 3' end. The universal nucleotide sequence is identical in each primer, and in one embodiment it includes a second sequencing primer sequence (also referred to as a Read 2 Primer in FIG. 2 (block vii). The region of random nucleotide sequence is used so that at least one primer should be present that is complementary to every sequence in the bisulfite-treated nucleic acid fragments. The number of random nucleotides that can be used to increase the probability of complete coverage to a desired level can be determined using routine methods, and can be from 6 to 12 random nucleotides, such as 9 random nucleotides. In one embodiment, the number of cycles is limited to no greater than 10 cycles, such as 9 cycles, 8 cycles, 7 cycles, 6 cycles, 5 cycles, 4 cycles, 3 cycles, 2 cycles, or 1 cycle. The result of linear amplification is amplified fragment-adapter molecules. An example of a fragment-adapter molecule is shown in FIG. 3. The fragment-adapter molecule 30 includes nucleotides originating from the transferred strand of the transposome complex 31 and 32, which includes a transposase index and a universal sequence that can be used for amplification and/or sequencing. The fragment-adapter molecule also includes the nucleotides originating from the genomic DNA of a nucleus 33, the region of random nucleotide sequence 34, and the universal nucleotide sequence 35.

Linear amplification is followed by an exponential amplification reaction, such as a PCR, to further modify the ends of the fragment-adapter molecule prior to immobilizing and sequencing. This step results in indexing of the fragment-adapter molecules by PCR (FIG. 1, block 19). The universal sequences 31, 32 and/or 35 present at ends of the fragment-adapter molecule can be used for the binding of universal anchor sequences which can serve as primers and be extended in an amplification reaction. Typically, two different primers are used. One primer hybridizes with universal sequences at the 3' end of one strand of the fragment-adapter molecule, and a second primer hybridizes with universal sequences at the 3' end of the other strand of the fragment-adapter molecule. Thus, the anchor sequence of each primer can be different. Suitable primers can each include additional universal sequences, such as a universal capture sequence, and another index sequence. Because each primer can include an index, this step results in the addition of one or two index sequences, e.g., a second and an optional third index. Fragment-adaptor molecules having the second and the optional third indexes are referred to as dual-index fragment-adapter molecules. The second and third indexes can be the reverse complements of each other, or the second and third indexes can have sequences that are not the reverse complements of each other. This second index sequence and optional third index is unique for each compartment in which the distributed indexed nuclei were placed before treatment with sodium bisulfite. The result of this PCR amplification is a plurality or library of fragment-adapter molecules having a structure similar or identical to the fragment-adapter molecule shown in FIG. 2, block vii.

In another embodiment, the modification includes subjecting the bisulfite-treated nucleic acid fragments to conditions that result in the ligation of additional sequences to both ends of the fragments. In one embodiment, blunt-ended ligation can be used. In another embodiment, the fragments are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of the bisulfite-treated nucleic acid fragments. Such enzymes can be used to add a single nucleotide 'A' to the blunt ended 3' terminus of each strand of the fragments. Thus, an 'A' could be added to the 3' terminus of each strand of the double-stranded target fragments by reaction with Taq or Klenow exo minus polymerase, while the additional sequences to be added to each end of the fragment can include a compatible 'T' overhang present on the 3' terminus of each region of double stranded nucleic acid to be added. This end modification also prevents self-ligation of the nucleic acids such that there is a bias towards formation of the bisulfite-treated nucleic acid fragments flanked by the sequences that are added in this embodiment.

Fragmentation of nucleic acid molecules by the methods described herein results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In one embodiment, the bisulfite-treated nucleic acid fragments are treated by first ligating identical universal adapters (also referred to as 'mismatched adaptors,' the general features of which are described in Gormley et al., U.S. Pat. No. 7,741,463, and Bignell et al., U.S. Pat. No. 8,053,192,) to the 5' and 3' ends of the bisulfite-treated nucleic acid fragments to form fragment-adapter molecules. In one embodiment, the universal adaptor includes all sequences necessary for sequencing, including immobilizing the fragment-adapter molecules on an array. Because the nucleic acids to be sequenced are from single cells, further amplification of the fragment-adapter molecules is helpful to achieve a sufficient number of fragment-adapter molecules for sequencing.

In another embodiment, when the universal adapter does not include all sequences necessary for sequencing, then a PCR step can be used to further modify the universal adapter present in each fragment-adapter molecule prior to immobilizing and sequencing. For instance, an initial primer extension reaction is carried out using a universal anchor sequence complementary to a universal sequence present in the fragment-adapter molecule, in which extension products complementary to both strands of each individual fragment-adapter molecule are formed. Typically, the PCR adds additional universal sequences, such as a universal capture sequence, and another index sequence. Because each primer can include an index, this step results in the addition of one or two index sequences, e.g., a second and an optional third index, and indexing of the fragment-adapter molecules by adapter ligation (FIG. 1, block 19). The resulting fragment-adaptor molecules are referred to as dual-index fragment-adapter molecules.

Figure 4:
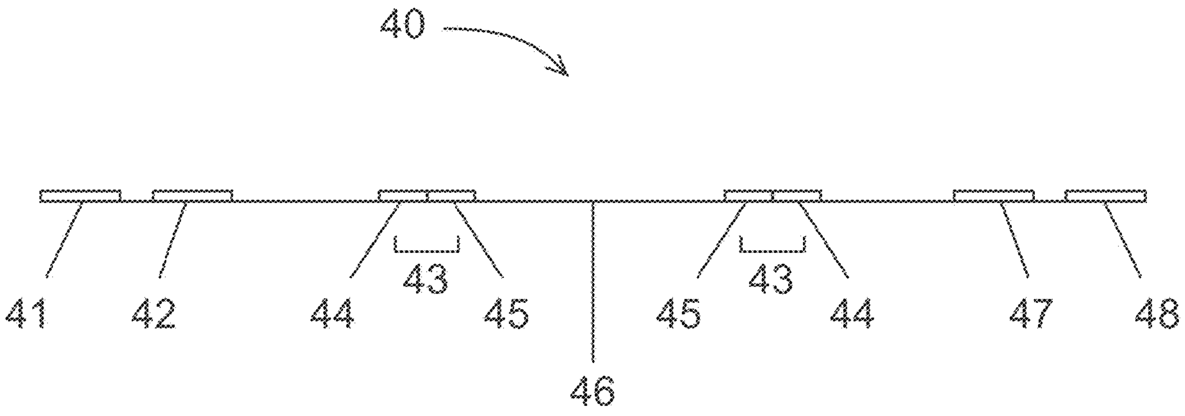
FIG. 4 shows a schematic drawing of an illustrative embodiment of a fragment-adapter molecule after addition of universal adapters.

After the universal adapters are added, either by a single step method of ligating a universal adaptor including all sequences necessary for sequencing, or by a two-step method of ligating a universal adapter and then PCR amplification to further modify the universal adapter, the final fragment-adapter molecule will include a universal capture sequence, a second index sequence, and an optional third index sequence. These indexes are analogous to the second and third indexes described in the production of dual-index fragment-adapters by linear amplification. The second and third indexes can be the reverse complements of each other, or the second and third indexes can have sequences that are not the reverse complements of each other. These second and optional third index sequences are unique for each compartment in which the distributed indexed nuclei were placed before treatment with sodium bisulfite. The result of adding universal adapters to each end is a plurality or library of fragment-adaptor molecules having a structure similar or identical to the fragment-adaptor molecule 40 shown in FIG. 4. The fragment-adapter molecule 40 includes a capture sequence 41 and 48, also referred to as a 3' flowcell adapter (e.g., P5) and 5' flowcell adapter (e.g., P7'), respectively, and an index 42 and 47, such as i5 and i7. The fragment-adapter molecule 40 also includes nucleotides originating from the transferred strand of the transposome complex 43, which includes a transposase index 44 and a universal sequence 45 that can be used for amplification and/or sequencing. The fragment-adapter molecule also includes the nucleotides originating from the genomic DNA of a nucleus 46.

The resulting dual-index fragment-adapter molecules collectively provide a library of nucleic acids that can be immobilized and then sequenced. The term library refers to the collection of fragments from single cells containing known universal sequences at their 3' and 5' ends.

After the bisulfite-treated nucleic acid fragments are modified to include additional nucleotides, the dual-index fragment-adapter molecules can be subjected to conditions that select for a predetermined size range, such as from 150 to 400 nucleotides in length, such as from 150 to 300 nucleotides. The resulting dual-index fragment-adapter molecules are pooled, and optionally can be subjected to a clean-up process to enhance the purity to the DNA molecules by removing at least a portion of unincorporated universal adapters or primers. Any suitable clean-up process may be used, such as electrophoresis, size exclusion chromatography, or the like. In some embodiments, solid phase reversible immobilization paramagnetic beads may be employed to separate the desired DNA molecules from unattached universal adapters or primers, and to select nucleic acids based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

The plurality of fragment-adapter molecules can be prepared for sequencing. After the fragment-adapter molecules are pooled they are immobilized and amplified prior to sequencing (FIG. 1, block 20). Methods for attaching fragment-adapter molecules from one or more sources to a substrate are known in the art. Likewise, methods for amplifying immobilized fragment-adapter molecules include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A pooled sample can be immobilized in preparation for sequencing. Sequencing can be performed as an array of single molecules, or can be amplified prior to sequencing. The amplification can be carried out using one or more immobilized primers. The immobilized primer(s) can be a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many embodiments the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of fragment-adapter molecules can then be contacted with the polished substrate such that individual fragment-adapter molecules will seed individual wells via interactions with primers attached to the gel material; however, the target nucleic acids will not occupy the interstitial regions due to absence or inactivity of the gel material. Amplification of the fragment-adapter molecules will be confined to the wells since absence or inactivity of gel in the interstitial regions prevents outward migration of the growing nucleic acid colony. The process can be conveniently manufactured, being scalable and utilizing conventional micro- or nano-fabrication methods.

Although the disclosure encompasses "solid-phase" amplification methods in which only one amplification primer is immobilized (the other primer usually being present in free solution), it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may include template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example, one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in WO 05/065814.

Certain embodiments of the disclosure may make use of solid supports comprised of an inert substrate or matrix (e.g. glass slides, polymer beads, etc.) which has been "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of fragment-adapter molecules is used to prepare clustered arrays of nucleic acid colonies, analogous to those described in U.S. Pub. No. 2005/0100900, U.S. Pat. No. 7,115,400, WO 00/18957 and WO 98/44151 by solid-phase amplification and more particularly solid phase isothermal amplification. The terms 'cluster' and 'colony' are used interchangeably herein to refer to a discrete site on a solid support including a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term "solid phase" or "surface" is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420. Due to the lower temperatures useful in the isothermal process, this is particularly preferred.

It will be appreciated that any of the amplification methodologies described herein or generally known in the art may be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, CA) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with the strand-displacing Phi 29 polymerase or Bst DNA polymerase large fragment, 5'->3' exo for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

Another polynucleotide amplification method that is useful in the present disclosure is Tagged PCR which uses a population of two-domain primers having a constant 5' region followed by a random 3' region as described, for example, in Grothues et al. Nucleic Acids Res. 21 (5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments, the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, amplification sites in an array can be, but need not be, entirely clonal. Rather, for some applications, an individual amplification site can be predominantly populated with amplicons from a first fragment-adapter molecule and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with fragment-adapter molecules from a solution and copies of the fragment-adapter molecules are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042.

Kinetic exclusion can exploit a relatively slow rate for initiating amplification (e.g. a slow rate of making a first copy of a fragment-adapter molecule) vs. a relatively rapid rate for making subsequent copies of the fragment-adapter molecule (or of the first copy of the fragment-adapter molecule). In the example of the previous paragraph, kinetic exclusion occurs due to the relatively slow rate of fragment-adapter molecule seeding (e.g. relatively slow diffusion or transport) vs. the relatively rapid rate at which amplification occurs to fill the site with copies of the fragment-adapter seed. In another exemplary embodiment, kinetic exclusion can occur due to a delay in the formation of a first copy of a fragment-adapter molecule that has seeded a site (e.g. delayed or slow activation) vs. the relatively rapid rate at which subsequent copies are made to fill the site. In this example, an individual site may have been seeded with several different fragment-adapter molecules (e.g. several fragment-adapter molecules can be present at each site prior to amplification). However, first copy formation for any given fragment-adapter molecule can be activated randomly such that the average rate of first copy formation is relatively slow compared to the rate at which subsequent copies are generated. In this case, although an individual site may have been seeded with several different fragment-adapter molecules, kinetic exclusion will allow only one of those fragment-adapter molecules to be amplified. More specifically, once a first fragment-adapter molecule has been activated for amplification, the site will rapidly fill to capacity with its copies, thereby preventing copies of a second fragment-adapter molecule from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a fragment-adapter molecule by the polymerase and extension of a primer by the polymerase using the fragment-adapter molecule as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

Following attachment of fragment-adapter molecules to a surface, the sequence of the immobilized and amplified fragment-adapter molecules is determined. Sequencing can be carried out using any suitable sequencing technique, and methods for determining the sequence of immobilized and amplified fragment-adapter molecules, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a fragment-adapter molecule can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

In one embodiment, a nucleotide monomer includes locked nucleic acids (LNAs) or bridged nucleic acids (BNAs). When the fragment-adapter molecules are produced using one or more cytosine-depleted nucleotide sequences, such as what results when cytosine-depleted nucleotide sequences are present in a transferred strand from a transposome complex, the melting temperature of a nucleotide monomer that hybridizes to a cytosine-depleted region is altered. The use of LNAs or BNAs in a nucleotide monomer increases hybridization strength between a nucleotide monomer and a sequencing primer sequence present on an immobilized fragment-adapter molecule.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102:5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can utilize detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis", Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the fragment-adapter molecule passes through a nanopore. The nanopore can be a synthetic pore or biological membrane protein, such as α-hemolysin. As the fragment-adapter molecule passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, both of which are incorporated herein by reference, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different fragment-adapter molecules are manipulated simultaneously. In particular embodiments, different fragment-adapter molecules can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the fragment-adapter molecules can be in an array format. In an array format, the fragment-adapter molecules can be typically bound to a surface in a spatially distinguishable manner. The fragment-adapter molecules can be bound by direct covalent attachment, attachment to a bead or other particle or binding to a polymerase or other molecule that is attached to the surface. The array can include a single copy of a fragment-adapter molecule at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/$cm^2$, 100 features/$cm^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of cm$^2$, in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system including components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. Ser. No. 13/273,666. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

During the practice of the methods described herein various compositions can result. For example, a dual-index fragment-adapter molecule, including a dual-index fragment-adapter molecule having a structure shown in FIG. 2 block vii or FIG. 4, and compositions including a dual-index fragment-adapter molecule, can result. A sequencing library of dual-index fragment-adapter molecules, including dual-index fragment-adapter molecules having a structure shown in FIG. 2 block vii or FIG. 4, and compositions including a sequencing library can result. Such a sequencing library can be bound to an array.

The present invention is illustrated by the following examples. It is to be understood that the particular examples, materials, amounts, and procedures are to be interpreted broadly in accordance with the scope and spirit of the invention as set forth herein.

EXAMPLES

Reagents Used in the Examples

- Phosphate Buffer Saline (PBS, Thermo Fisher, Cat. 10010023)
- 0.25% Trypsin (Thermo Fisher, Cat. 15050057)
- Tris (Fisher, Cat. T1503)
- HCl (Fisher, Cat. A144)
- NaCl (Fisher, Cat. M-11624)
- MgCl2 (Sigma, Cat. M8226)
- Igepal® CA-630 (Sigma, I8896)
- Protease Inhibitors (Roche, Cat. 11873580001)
- PCR-Clean ddH2O
- Lithium 3,5-diiodosalicylic acid (Sigma, Cat. D3635)—LAND method only
- Formaldehyde (Sigma, Cat. F8775)—xSDS method only
- Glycine (Sigma, Cat. G8898)—xSDS method only
- NEBuffer 2.1 (NEB, Cat. B7202)—xSDS method only
- SDS (Sigma, Cat. L3771)—xSDS method only
- Triton™ X-100 (Sigma, Cat. 9002-93-1)—xSDS method only
- DAPI (Thermo Fisher, Cat. D1306)
- TD buffer from Nextera® kit (Illumina, Cat. FC-121-1031)
- 96 Indexed Cytosine-Depleted Transposomes (assembled using published methods, sequences shown in Table 1)
- 9-Nucleotide Random Primer (Table 2)
- 10 mM dNTP Mix (NEB, Cat. N0447)
- Klenow (3'->5' Exo-) Polymerase (Enzymatics, Cat. P7010-LC-L)
- 200 Proof Ethanol
- Indexed i5 and i7 PCR primers (Table 3)
- Kapa HiFi™ HotStart ReadyMix
- SYBR® Green (FMC BioProducts, Cat. 50513)
- QIAquick® PCR purification kit (Qiagen, Cat. 28104)
- dsDNA High Sensitivity Qubit® (Thermo Fisher, Cat. Q32851)
- High Sensitivity Bioanalyzer kit (Agilent, Cat. 5067-4626)
- NextSeq sequencing kit (High or Mid 150-cycle)
- Unmethylated Lambda DNA (Promega, Cat. D1521)
- HiSeq® 2500 Sequencing Kit (Illumina)
- HiSeq® X Sequencing Kit (Illumina)
- EZ-96 DNA Methylation MagPrep Kit (Zymo Research, Cat D5040)
- Custom LNA Sequencing primers (Table 4)
- Polyethylene glycol (PEG)
- SPRI Beads Equipment Used in the Examples

- 35 μM Cell Strainer (BD Biosciences, Cat. 352235)
- 96-well plate compatible magnetic rack
- Sony SH800 cell sorter (Sony Biotechnology, Cat. SH800) or other FACS instrument capable of DAPI based single nuclei sorting
- CFX Connect RT Thermal Cycler (Bio-Rad, Cat. 1855200) or other real time thermocycler
- Thermomixer
- Qubit® 2.0 Fluorometer (Thermo Fisher, Cat. Q32866)
- 2100 Bioanalyzer (Agilent, Cat. G2939A)
- NextSeq® 500 (Illumina, Cat. SY-415-1001-1)
- HiSeq® 2500 (Illumina)
- HiSeq® X (Illumina)

Oligonucleotides Used in the Examples

TABLE 1 sciMET Transposase-loaded Oligos (5'-3')
Reverse Compliment: (5phos) CTGTCTCTTATACACATCT SEQ ID NO: 97

| Name | i5_bsPCR | index | | i5_Tn5 |
|---|---|---|---|---|
| sciMET_Tn5_1 SEQ ID NO: 1 | GGTGTAGTGGGTTTGG | GTTAAGAGGAA | TGGTAGAGAGGGTG | AGATGTGTATAAGAGACAG |
| sciMET_Tn5_2 SEQ ID NO: 2 | GGTGTAGTGGGTTTGG | AGTAGGAAGAT | TGGTAGAGAGGGTG | AGATGTGTATAAGAGACAG |

TABLE 1-continued

| sciMET Transposase-loaded Oligos (5'-3') Reverse Compliment: (5phos) CTGTCTCTTATACACATCT SEQ ID NO: 97 | | | | |
|---|---|---|---|---|
| Name | i5_bsPCR | index | | i5_Tn5 |
| sciMET_Tn5_3 SEQ ID NO: 3 | GGTGTAGTGGGTTTGG | GAATTAGGTGT | TGGTAGAGAGGGTG | AGATGTGTATAAGAGACAG |
| sciMET_Tn5_4 SEQ ID NO: 4 | GGTGTAGTGGGTTTGG | GGAGATTAATG | TGGTAGAGAGGGTG | AGATGTGTATAAGAGACAG |
| sciMET_Tn5_5 SEQ ID NO: 5 | GGTGTAGTGGGTTTGG | TATTGTGGAAT | TGGTAGAGAGGGTG | AGATGTGTATAAGAGACAG |
| sciMET_Tn5_6 SEQ ID NO: 6 | GGTGTAGTGGGTTTGG | ATATAGATGAT | TGGTAGAGAGGGTG | AGATGTGTATAAGAGACAG |
| sciMET_Tn5_7 SEQ ID NO: 7 | GGTGTAGTGGGTTTGG | GTAAGAGGAAT | TGGTAGAGAGGGTG | AGATGTGTATAAGAGACAG |
| sciMET_Tn5_8 SEQ ID NO: 8 | GGTGTAGTGGGTTTGG | GAGAGTTATTG | TGGTAGAGAGGGTG | AGATGTGTATAAGAGACAG |
| sciMET_Tn5_9 SEQ ID NO: 9 | GGTGTAGTGGGTTTGG | AGTTAGTGTGA | TGGTAGAGAGGGTG | AGATGTGTATAAGAGACAG |
| sciMET_Tn5_10 SEQ ID NO: 10 | GGTGTAGTGGGTTTGG | GATATAGAATT | TGGTAGAGAGGGTG | AGATGTGTATAAGAGACAG |
| sciMET_Tn5_11 SEQ ID NO: 11 | GGTGTAGTGGGTTTGG | AAGGAAGTGAA | TGGTAGAGAGGGTG | AGATGTGTATAAGAGACAG |
| sciMET_Tn5_12 SEQ ID NO: 12 | GGTGTAGTGGGTTTGG | AATAAGGAAGG | TGGTAGAGAGGGTG | AGATGTGTATAAGAGACAG |
| sciMET_Tn5_13 SEQ ID NO: 13 | GGTGTAGTGGGTTTGG | GTATGGATATA | TGGTAGAGAGGGTG | AGATGTGTATAAGAGACAG |
| sciMET_Tn5_14 SEQ ID NO: 14 | GGTGTAGTGGGTTTGG | TTAGATAATGA | TGGTAGAGAGGGTG | AGATGTGTATAAGAGACAG |
| sciMET_Tn5_15 SEQ ID NO: 15 | GGTGTAGTGGGTTTGG | GGTGTTGTAAT | TGGTAGAGAGGGTG | AGATGTGTATAAGAGACAG |
| sciMET_Tn5_16 SEQ ID NO: 16 | GGTGTAGTGGGTTTGG | GAAGTGGAGAG | TGGTAGAGAGGGTG | AGATGTGTATAAGAGACAG |
| sciMET_Tn5_17 SEQ ID NO: 17 | GGTGTAGTGGGTTTGG | TTGAGTGGTAG | TGGTAGAGAGGGTG | AGATGTGTATAAGAGACAG |
| sciMET_Tn5_18 SEQ ID NO: 18 | GGTGTAGTGGGTTTGG | GATAATGGTGA | TGGTAGAGAGGGTG | AGATGTGTATAAGAGACAG |
| sciMET_Tn5_19 SEQ ID NO: 19 | GGTGTAGTGGGTTTGG | GTGTTAATGGA | TGGTAGAGAGGGTG | AGATGTGTATAAGAGACAG |
| sciMET_Tn5_20 SEQ ID NO: 20 | GGTGTAGTGGGTTTGG | TAGGAATGGTG | TGGTAGAGAGGGTG | AGATGTGTATAAGAGACAG |
| sciMET_Tn5_21 SEQ ID NO: 21 | GGTGTAGTGGGTTTGG | ATGTATGGATA | TGGTAGAGAGGGTG | AGATGTGTATAAGAGACAG |
| sciMET_Tn5_22 SEQ ID NO: 22 | GGTGTAGTGGGTTTGG | TGATTGTTGGT | TGGTAGAGAGGGTG | AGATGTGTATAAGAGACAG |
| sciMET_Tn5_23 SEQ ID NO: 23 | GGTGTAGTGGGTTTGG | AAGAGAATTAT | TGGTAGAGAGGGTG | AGATGTGTATAAGAGACAG |
| sciMET_Tn5_24 SEQ ID NO: 24 | GGTGTAGTGGGTTTGG | AATGGTTGGTA | TGGTAGAGAGGGTG | AGATGTGTATAAGAGACAG |
| sciMET_Tn5_25 SEQ ID NO: 25 | GGTGTAGTGGGTTTGG | GGTTAATTGAG | TGGTAGAGAGGGTG | AGATGTGTATAAGAGACAG |
| sciMET_Tn5_26 SEQ ID NO: 26 | GGTGTAGTGGGTTTGG | GTATAATAGTT | TGGTAGAGAGGGTG | AGATGTGTATAAGAGACAG |
| sciMET_Tn5_27 SEQ ID NO: 27 | GGTGTAGTGGGTTTGG | TTAGTTGAATT | TGGTAGAGAGGGTG | AGATGTGTATAAGAGACAG |

TABLE 1-continued

| sciMET Transposase-loaded Oligos (5'-3') Reverse Compliment: (5phos) CTGTCTCTTATACACATCT SEQ ID NO: 97 | | | | |
|---|---|---|---|---|
| Name | i5_bsPCR | index | | i5_Tn5 |
| sciMET_Tn5_28 SEQ ID NO: 28 | GGTGTAGTGGGTTTGG | TTGGTGAAGGT | TGGTAGAGAGGGTG | AGATGTGTATAAGAGACAG |
| sciMET_Tn5_29 SEQ ID NO: 29 | GGTGTAGTGGGTTTGG | TTAATATTGAA | TGGTAGAGAGGGTG | AGATGTGTATAAGAGACAG |
| sciMET_Tn5_30 SEQ ID NO: 30 | GGTGTAGTGGGTTTGG | GTTAGAATTGG | TGGTAGAGAGGGTG | AGATGTGTATAAGAGACAG |
| sciMET_Tn5_31 SEQ ID NO: 31 | GGTGTAGTGGGTTTGG | GTTATTAATTA | TGGTAGAGAGGGTG | AGATGTGTATAAGAGACAG |
| sciMET_Tn5_32 SEQ ID NO: 32 | GGTGTAGTGGGTTTGG | GATTGGTAAGA | TGGTAGAGAGGGTG | AGATGTGTATAAGAGACAG |
| sciMET_Tn5_33 SEQ ID NO: 33 | GGTGTAGTGGGTTTGG | TGAAGTATTGT | TGGTAGAGAGGGTG | AGATGTGTATAAGAGACAG |
| sciMET_Tn5_34 SEQ ID NO: 34 | GGTGTAGTGGGTTTGG | GATGGATTATG | TGGTAGAGAGGGTG | AGATGTGTATAAGAGACAG |
| sciMET_Tn5_35 SEQ ID NO: 35 | GGTGTAGTGGGTTTGG | ATTAGTATATT | TGGTAGAGAGGGTG | AGATGTGTATAAGAGACAG |
| sciMET_Tn5_36 SEQ ID NO: 36 | GGTGTAGTGGGTTTGG | GTAGGTGTGGT | TGGTAGAGAGGGTG | AGATGTGTATAAGAGACAG |
| sciMET_Tn5_37 SEQ ID NO: 37 | GGTGTAGTGGGTTTGG | AGTTGAATGTA | TGGTAGAGAGGGTG | AGATGTGTATAAGAGACAG |
| sciMET_Tn5_38 SEQ ID NO: 38 | GGTGTAGTGGGTTTGG | ATTGTGAGATA | TGGTAGAGAGGGTG | AGATGTGTATAAGAGACAG |
| sciMET_Tn5_39 SEQ ID NO: 39 | GGTGTAGTGGGTTTGG | TTGTGGTGAGT | TGGTAGAGAGGGTG | AGATGTGTATAAGAGACAG |
| sciMET_Tn5_40 SEQ ID NO: 40 | GGTGTAGTGGGTTTGG | TTAAGTTGGTT | TGGTAGAGAGGGTG | AGATGTGTATAAGAGACAG |
| sciMET_Tn5_41 SEQ ID NO: 41 | GGTGTAGTGGGTTTGG | TATAATAATAT | TGGTAGAGAGGGTG | AGATGTGTATAAGAGACAG |
| sciMET_Tn5_42 SEQ ID NO: 42 | GGTGTAGTGGGTTTGG | AAGGTATGAGT | TGGTAGAGAGGGTG | AGATGTGTATAAGAGACAG |
| sciMET_Tn5_43 SEQ ID NO: 43 | GGTGTAGTGGGTTTGG | AGGATTATAAG | TGGTAGAGAGGGTG | AGATGTGTATAAGAGACAG |
| sciMET_Tn5_44 SEQ ID NO: 44 | GGTGTAGTGGGTTTGG | AGAGTTAGGTT | TGGTAGAGAGGGTG | AGATGTGTATAAGAGACAG |
| sciMET_Tn5_45 SEQ ID NO: 45 | GGTGTAGTGGGTTTGG | ATGGATAGTAT | TGGTAGAGAGGGTG | AGATGTGTATAAGAGACAG |
| sciMET_Tn5_46 SEQ ID NO: 46 | GGTGTAGTGGGTTTGG | ATATTATGTTG | TGGTAGAGAGGGTG | AGATGTGTATAAGAGACAG |
| sciMET_Tn5_47 SEQ ID NO: 47 | GGTGTAGTGGGTTTGG | GGTGGAGATAG | TGGTAGAGAGGGTG | AGATGTGTATAAGAGACAG |
| sciMET_Tn5_48 SEQ ID NO: 48 | GGTGTAGTGGGTTTGG | TGGTGGTAGTG | TGGTAGAGAGGGTG | AGATGTGTATAAGAGACAG |
| sciMET_Tn5_49 SEQ ID NO: 49 | GGTGTAGTGGGTTTGG | AGGTGAGAAGT | TGGTAGAGAGGGTG | AGATGTGTATAAGAGACAG |
| sciMET_Tn5_50 SEQ ID NO: 50 | GGTGTAGTGGGTTTGG | TAGGAGGTTGT | TGGTAGAGAGGGTG | AGATGTGTATAAGAGACAG |
| sciMET_Tn5_51 SEQ ID NO: 51 | GGTGTAGTGGGTTTGG | TGTATAGGTAT | TGGTAGAGAGGGTG | AGATGTGTATAAGAGACAG |
| sciMET_Tn5_52 SEQ ID NO: 52 | GGTGTAGTGGGTTTGG | TGTTATGTAGA | TGGTAGAGAGGGTG | AGATGTGTATAAGAGACAG |

TABLE 1-continued

| sciMET Transposase-loaded Oligos (5'-3')<br>Reverse Compliment: (5phos) CTGTCTCTTATACACATCT SEQ ID NO: 97 | | | | |
|---|---|---|---|---|
| Name | i5_bsPCR | index | | i5_Tn5 |
| sciMET_Tn5_53 SEQ ID NO: 53 | GGTGTAGTGGGTTTGG | TGGAAGGTATG | TGGTAGAGAGGGTG | AGATGTGTATAAGAGACAG |
| sciMET_Tn5_54 SEQ ID NO: 54 | GGTGTAGTGGGTTTGG | AATGTAAGGAG | TGGTAGAGAGGGTG | AGATGTGTATAAGAGACAG |
| sciMET_Tn5_55 SEQ ID NO: 55 | GGTGTAGTGGGTTTGG | GTTATGTTAAG | TGGTAGAGAGGGTG | AGATGTGTATAAGAGACAG |
| sciMET_Tn5_56 SEQ ID NO: 56 | GGTGTAGTGGGTTTGG | TGTTATAGGTG | TGGTAGAGAGGGTG | AGATGTGTATAAGAGACAG |
| sciMET_Tn5_57 SEQ ID NO: 57 | GGTGTAGTGGGTTTGG | AAGGAGAATTG | TGGTAGAGAGGGTG | AGATGTGTATAAGAGACAG |
| sciMET_Tn5_58 SEQ ID NO: 58 | GGTGTAGTGGGTTTGG | AGAGGTGGAAG | TGGTAGAGAGGGTG | AGATGTGTATAAGAGACAG |
| sciMET_Tn5_59 SEQ ID NO: 59 | GGTGTAGTGGGTTTGG | GATTAGGTGTA | TGGTAGAGAGGGTG | AGATGTGTATAAGAGACAG |
| sciMET_Tn5_60 SEQ ID NO: 60 | GGTGTAGTGGGTTTGG | ATTATATAAGA | TGGTAGAGAGGGTG | AGATGTGTATAAGAGACAG |
| sciMET_Tn5_61 SEQ ID NO: 61 | GGTGTAGTGGGTTTGG | GAGAATATGGT | TGGTAGAGAGGGTG | AGATGTGTATAAGAGACAG |
| sciMET_Tn5_62 SEQ ID NO: 62 | GGTGTAGTGGGTTTGG | GGATTGAGAGG | TGGTAGAGAGGGTG | AGATGTGTATAAGAGACAG |
| sciMET_Tn5_63 SEQ ID NO: 63 | GGTGTAGTGGGTTTGG | ATTATGGTGGT | TGGTAGAGAGGGTG | AGATGTGTATAAGAGACAG |
| sciMET_Tn5_64 SEQ ID NO: 64 | GGTGTAGTGGGTTTGG | GAAGGAAGTTA | TGGTAGAGAGGGTG | AGATGTGTATAAGAGACAG |
| sciMET_Tn5_65 SEQ ID NO: 65 | GGTGTAGTGGGTTTGG | GAATATGTAAG | TGGTAGAGAGGGTG | AGATGTGTATAAGAGACAG |
| sciMET_Tn5_66 SEQ ID NO: 66 | GGTGTAGTGGGTTTGG | TAGTTAATATT | TGGTAGAGAGGGTG | AGATGTGTATAAGAGACAG |
| sciMET_Tn5_67 SEQ ID NO: 67 | GGTGTAGTGGGTTTGG | TGAATGAATAG | TGGTAGAGAGGGTG | AGATGTGTATAAGAGACAG |
| sciMET_Tn5_68 SEQ ID NO: 68 | GGTGTAGTGGGTTTGG | AGGATGGATTA | TGGTAGAGAGGGTG | AGATGTGTATAAGAGACAG |
| sciMET_Tn5_69 SEQ ID NO: 69 | GGTGTAGTGGGTTTGG | AAGTGTATAGA | TGGTAGAGAGGGTG | AGATGTGTATAAGAGACAG |
| sciMET_Tn5_70 SEQ ID NO: 70 | GGTGTAGTGGGTTTGG | GAGGTTGAAGA | TGGTAGAGAGGGTG | AGATGTGTATAAGAGACAG |
| sciMET_Tn5_71 SEQ ID NO: 71 | GGTGTAGTGGGTTTGG | TGTGTAATAGG | TGGTAGAGAGGGTG | AGATGTGTATAAGAGACAG |
| sciMET_Tn5_72 SEQ ID NO: 72 | GGTGTAGTGGGTTTGG | TTGATTAGAGA | TGGTAGAGAGGGTG | AGATGTGTATAAGAGACAG |
| sciMET_Tn5_73 SEQ ID NO: 73 | GGTGTAGTGGGTTTGG | TATGTGTGTGG | TGGTAGAGAGGGTG | AGATGTGTATAAGAGACAG |
| sciMET_Tn5_74 SEQ ID NO: 74 | GGTGTAGTGGGTTTGG | GAGATGAGAAT | TGGTAGAGAGGGTG | AGATGTGTATAAGAGACAG |
| sciMET_Tn5_75 SEQ ID NO: 75 | GGTGTAGTGGGTTTGG | TGGTGAAGTGA | TGGTAGAGAGGGTG | AGATGTGTATAAGAGACAG |
| sciMET_Tn5_76 SEQ ID NO: 76 | GGTGTAGTGGGTTTGG | GTGGTAGGATG | TGGTAGAGAGGGTG | AGATGTGTATAAGAGACAG |
| sciMET_Tn5_77 SEQ ID NO: 77 | GGTGTAGTGGGTTTGG | TGTAGGTGATA | TGGTAGAGAGGGTG | AGATGTGTATAAGAGACAG |

TABLE 1-continued

| sciMET Transposase-loaded Oligos (5'-3') Reverse Compliment: (5phos) CTGTCTCTTATACACATCT SEQ ID NO: 97 | | | | |
|---|---|---|---|---|
| Name | i5_bsPCR | index | | i5_Tn5 |
| sciMET_Tn5_78 SEQ ID NO: 78 | GGTGTAGTGGGTTTGG | GTAAGGTGTGA | TGGTAGAGAGGGTG | AGATGTGTATAAGAGACAG |
| sciMET_Tn5_79 SEQ ID NO: 79 | GGTGTAGTGGGTTTGG | AGAAGAGAGTG | TGGTAGAGAGGGTG | AGATGTGTATAAGAGACAG |
| sciMET_Tn5_80 SEQ ID NO: 80 | GGTGTAGTGGGTTTGG | GGATGTTGTAT | TGGTAGAGAGGGTG | AGATGTGTATAAGAGACAG |
| sciMET_Tn5_81 SEQ ID NO: 81 | GGTGTAGTGGGTTTGG | AAGTTATATAA | TGGTAGAGAGGGTG | AGATGTGTATAAGAGACAG |
| sciMET_Tn5_82 SEQ ID NO: 82 | GGTGTAGTGGGTTTGG | TGGAATTAAGT | TGGTAGAGAGGGTG | AGATGTGTATAAGAGACAG |
| sciMET_Tn5_83 SEQ ID NO: 83 | GGTGTAGTGGGTTTGG | TAATGAGAGGA | TGGTAGAGAGGGTG | AGATGTGTATAAGAGACAG |
| sciMET_Tn5_84 SEQ ID NO: 84 | GGTGTAGTGGGTTTGG | ATAATTGATGG | TGGTAGAGAGGGTG | AGATGTGTATAAGAGACAG |
| sciMET_Tn5_85 SEQ ID NO: 85 | GGTGTAGTGGGTTTGG | TGTGAAGAGTA | TGGTAGAGAGGGTG | AGATGTGTATAAGAGACAG |
| sciMET_Tn5_86 SEQ ID NO: 86 | GGTGTAGTGGGTTTGG | GATGAATATGT | TGGTAGAGAGGGTG | AGATGTGTATAAGAGACAG |
| sciMET_Tn5_87 SEQ ID NO: 87 | GGTGTAGTGGGTTTGG | TGAGGATAGAT | TGGTAGAGAGGGTG | AGATGTGTATAAGAGACAG |
| sciMET_Tn5_88 SEQ ID NO: 88 | GGTGTAGTGGGTTTGG | ATTAATTAGAG | TGGTAGAGAGGGTG | AGATGTGTATAAGAGACAG |
| sciMET_Tn5_89 SEQ ID NO: 89 | GGTGTAGTGGGTTTGG | GGAGAGATGGA | TGGTAGAGAGGGTG | AGATGTGTATAAGAGACAG |
| sciMET_Tn5_90 SEQ ID NO: 90 | GGTGTAGTGGGTTTGG | TAATTGAGGAA | TGGTAGAGAGGGTG | AGATGTGTATAAGAGACAG |
| sciMET_Tn5_91 SEQ ID NO: 91 | GGTGTAGTGGGTTTGG | TTGGAATTAAT | TGGTAGAGAGGGTG | AGATGTGTATAAGAGACAG |
| sciMET_Tn5_92 SEQ ID NO: 92 | GGTGTAGTGGGTTTGG | AATGTTATTGT | TGGTAGAGAGGGTG | AGATGTGTATAAGAGACAG |
| sciMET_Tn5_93 SEQ ID NO: 93 | GGTGTAGTGGGTTTGG | GTAGTTATTAG | TGGTAGAGAGGGTG | AGATGTGTATAAGAGACAG |
| sciMET_Tn5_94 SEQ ID NO: 94 | GGTGTAGTGGGTTTGG | TATATTGTGAG | TGGTAGAGAGGGTG | AGATGTGTATAAGAGACAG |
| sciMET_Tn5_95 SEQ ID NO: 95 | GGTGTAGTGGGTTTGG | GTGTAGGATAG | TGGTAGAGAGGGTG | AGATGTGTATAAGAGACAG |
| sciMET_Tn5_96 SEQ ID NO: 96 | GGTGTAGTGGGTTTGG | AGAGAAGTTGG | TGGTAGAGAGGGTG | AGATGTGTATAAGAGACAG |

TABLE 2

| sciMET 9-nulceotide Random Primer (5'-3') | |
|---|---|
| Name | Sequence |
| sciMET_N9_ IPE2 SEQ ID NO: 98 | GGAGTTCAGACGTGTGCTCTTCCGATCTN NNNNNNNN |

TABLE 3

| sciMET PCR primers (5'-3') | |
|---|---|
| Name | Sequence |
| sciMET_i7_1 SEQ ID NO: 99 | CAAGCAGAAGACGGCATACGAGATcaagatgccgGTGACTGGAGTTCAGACGTGTGCTCTTCCGATCT |
| sciMET_i7_2 SEQ ID NO: 100 | CAAGCAGAAGACGGCATACGAGATaacgtctagtGTGACTGGAGTTCAGACGTGTGCTCTTCCGATCT |
| sciMET_i7_3 SEQ ID NO: 101 | CAAGCAGAAGACGGCATACGAGATaggtatactcGTGACTGGAGTTCAGACGTGTGCTCTTCCGATCT |
| sciMET_i7_4 SEQ ID NO: 102 | CAAGCAGAAGACGGCATACGAGATttcataggacGTGACTGGAGTTCAGACGTGTGCTCTTCCGATCT |
| sciMET_i7_5 SEQ ID NO: 103 | CAAGCAGAAGACGGCATACGAGATggaggcctccGTGACTGGAGTTCAGACGTGTGCTCTTCCGATCT |
| sciMET_i7_6 SEQ ID NO: 104 | CAAGCAGAAGACGGCATACGAGATttcaatataaGTGACTGGAGTTCAGACGTGTGCTCTTCCGATCT |
| sciMET_i7_7 SEQ ID NO: 105 | CAAGCAGAAGACGGCATACGAGATacgtcatataGTGACTGGAGTTCAGACGTGTGCTCTTCCGATCT |
| sciMET_i7_8 SEQ ID NO: 106 | CAAGCAGAAGACGGCATACGAGATttgaccaggaGTGACTGGAGTTCAGACGTGTGCTCTTCCGATCT |
| sciMET_i7_9 SEQ ID NO: 107 | CAAGCAGAAGACGGCATACGAGATcggttgcgcgGTGACTGGAGTTCAGACGTGTGCTCTTCCGATCT |
| sciMET_i7_10 SEQ ID NO: 108 | CAAGCAGAAGACGGCATACGAGATcaaggaggtcGTGACTGGAGTTCAGACGTGTGCTCTTCCGATCT |
| sciMET_i7_11 SEQ ID NO: 109 | CAAGCAGAAGACGGCATACGAGATttacgatgaaGTGACTGGAGTTCAGACGTGTGCTCTTCCGATCT |
| sciMET_i7_12 SEQ ID NO: 110 | CAAGCAGAAGACGGCATACGAGATttgctggcatGTGACTGGAGTTCAGACGTGTGCTCTTCCGATCT |
| sciMET_i7_13 SEQ ID NO: 111 | CAAGCAGAAGACGGCATACGAGATaatactcttcGTGACTGGAGTTCAGACGTGTGCTCTTCCGATCT |
| sciMET_i7_14 SEQ ID NO: 112 | CAAGCAGAAGACGGCATACGAGATccaactaaccGTGACTGGAGTTCAGACGTGTGCTCTTCCGATCT |
| sciMET_i7_15 SEQ ID NO: 113 | CAAGCAGAAGACGGCATACGAGATtatcctcaatGTGACTGGAGTTCAGACGTGTGCTCTTCCGATCT |
| sciMET_i7_16 SEQ ID NO: 114 | CAAGCAGAAGACGGCATACGAGATgccgtcgcgtGTGACTGGAGTTCAGACGTGTGCTCTTCCGATCT |
| sciMET_i7_17 SEQ ID NO: 115 | CAAGCAGAAGACGGCATACGAGATccgctgcttcGTGACTGGAGTTCAGACGTGTGCTCTTCCGATCT |
| sciMET_i7_18 SEQ ID NO: 116 | CAAGCAGAAGACGGCATACGAGATtgaccgaatcGTGACTGGAGTTCAGACGTGTGCTCTTCCGATCT |
| sciMET_i7_19 SEQ ID NO: 117 | CAAGCAGAAGACGGCATACGAGATgtctccagagGTGACTGGAGTTCAGACGTGTGCTCTTCCGATCT |
| sciMET_i7_20 SEQ ID NO: 118 | CAAGCAGAAGACGGCATACGAGATaatgctagtcGTGACTGGAGTTCAGACGTGTGCTCTTCCGATCT |
| sciMET_i7_21 SEQ ID NO: 119 | CAAGCAGAAGACGGCATACGAGATgacgacctgcGTGACTGGAGTTCAGACGTGTGCTCTTCCGATCT |
| sciMET_i7_22 SEQ ID NO: 120 | CAAGCAGAAGACGGCATACGAGATagagccagccGTGACTGGAGTTCAGACGTGTGCTCTTCCGATCT |
| sciMET_i7_23 SEQ ID NO: 121 | CAAGCAGAAGACGGCATACGAGATccaggccgcaGTGACTGGAGTTCAGACGTGTGCTCTTCCGATCT |
| sciMET_i7_24 SEQ ID NO: 122 | CAAGCAGAAGACGGCATACGAGATcaggtatggaGTGACTGGAGTTCAGACGTGTGCTCTTCCGATCT |
| sciMET_i7_1 SEQ ID NO: 123 | AATGATACGGCGACCACCGAGATCTACACgtatcatcgaGGTGTAGTGGGTTTGG |

TABLE 3-continued

| sciMET PCR primers (5'-3') | |
|---|---|
| Name | Sequence |
| sciMET_i7_2 SEQ ID NO: 124 | AATGATACGGCGACCACCGAGATCTACACccgcgattatGGTGTAGTGGGTTTGG |
| sciMET_i7_3 SEQ ID NO: 125 | AATGATACGGCGACCACCGAGATCTACACattcaggtacGGTGTAGTGGGTTTGG |
| sciMET_i7_4 SEQ ID NO: 126 | AATGATACGGCGACCACCGAGATCTACACatggaattggGGTGTAGTGGGTTTGG |
| sciMET_i7_5 SEQ ID NO: 127 | AATGATACGGCGACCACCGAGATCTACACgacgaagcgtGGTGTAGTGGGTTTGG |
| sciMET_i7_6 SEQ ID NO: 128 | AATGATACGGCGACCACCGAGATCTACACcttgcagtagGGTGTAGTGGGTTTGG |
| sciMET_i7_7 SEQ ID NO: 129 | AATGATACGGCGACCACCGAGATCTACACcttggtaatgGGTGTAGTGGGTTTGG |
| sciMET_i7_8 SEQ ID NO: 130 | AATGATACGGCGACCACCGAGATCTACACcaagtcgaccGGTGTAGTGGGTTTGG |

TABLE 4

| sciMET Sequencing Primers (LNA, 5'-3') | |
|---|---|
| Name | Sequence |
| sciMET_Read1 SEQ ID NO: 131 | TGGTAGAGAGGGTG AGATGTGTATAAGAGATAG |
| sciMET_Iindex1 SEQ ID NO: 132 | CTATCTCTTATACACATCT CACCCTCTCTACCA |

Example 1

Preparation of Unmethylated Control Lambda DNA

One hundred nanograms of unmethylated Lambda DNA, 5 uL of 2X TD Buffer, 5 uL 5 NIB buffer (10 mM Tris-HCl pH7.4, 10 MM NaCl, 3 mM MgCl2, 0.1% Igepal®, 1× protease inhibitors), and 4 μL 500 nM of uniquely indexed cytosine-depleted transposome were combined. The mixture was incubated for 20 minutes at 55° C., and then purified using QIAquick® PCR Purification column and eluted in 30 μL of EB.

The concentration of DNA was quantified with a dsDNA High Sensitivity Qubit 2.0 Fluorometer using 2 uL of the mixture. The concentration was diluted to 17.95 pg/uL, which simulates the genomic mass of roughly 5 human cells.

Example 2

Preparation of 18% PEG SPRI Bead Mixture

Sera-Mag beads (1 ml) were aliquoted to a low-bind 1.5 mL tube, and then placed on a magnetic stand until supernatant is cleared. The beads were washed with a solution of 500 uL 10 mM Tris-HCl, pH 8.0, and the solution removed after the supernatant cleared, and this wash step was repeated for a total of four washes. The beads were resuspended in the following mixture: 18% PEG 8000 (by mass), 1M NaCl, 10 mM Tris-HCl, pH 8.0, 1 mM EDTA, 0.05% Tween-20; incubated at room temperature with mild agitation for at least an hour, and then 18% PEG SPRI beads were stored at 4° C. The beads were allowed to reach room temperature before use.

Example 3

Preparation of Nuclei Using Lithium 3,5-Diiodosalicylic Acid (LAND) or SDS (xSDS)

A. LAND Method of Nuclei Preparation & Nucleosome Depletion

If the cells were in a suspension cell culture, the culture was gently triturated to break up cell clumps, the cells were pelleted by spinning at 500×g for 5 minutes at 4° C., and washed with 500 μL ice cold PBS.

If the cells were in an adherent cell culture, media was aspirated and the cells washed with 10 mL of PBS at 37° C., and then enough 0.25% Trypsin at 37° C. was added to cover the monolayer. After incubating at 37° C. for 5 minutes or until 90% of cells were no longer adhering to the surface, 37° *C. media* was added at 1:1 ratio to quench Trypsin. The cells were pelleted by spinning at 500×g for 5 minutes at 4° C., and then washed with 500 μL ice cold PBS.

The cells from either suspension cell culture or adherent cell culture were pelleted by spinning at 500×g for 5 minutes, and then resuspended in 200 μL 12.5 mM LIS in NIB buffer (2.5 μL 1M LIS+197.5 μL NIB buffer). After incubating on ice for 5 minutes, 800 μL NIB buffer was added. The cells were gently passed through a 35 μM cell strainer, and 5 μL DAPI (5 mg/mL) was added.

B. xSDS Method of Nuclei Preparation & Nucleosome Depletion

If the cells were in a suspension cell culture, the medium was gently triturated to break up cell clumps. To 10 mL of cells in media 406 μL of 37% formaldehyde were added and incubated at room temp for 10 minutes with gentle shaking. Eight hundred microliters of 2.5 M Glycine were added to the cells and incubated on ice for 5 minutes, and then centrifuged at 550×g for 8 minutes at 4° C. After washing with 10 mL of ice cold PBS, the cells were resuspended in 5 mL of ice cold NIB (10 mM TrisHCl pH7.4, 10 mM NaCl, 3 mM MgCl2, 0.1% Igepal®, 1×protease inhibitors), and incubated on ice for 20 minutes with gentle mixing.

If the cells were in an adherent cell culture, media was aspirated and the cells washed with 10 mL of PBS at 37° C., and then enough 0.25% Trypsin at 37° C. was added to cover the monolayer. After incubating at 37° C. for 5 minutes or until 90% of cells were no longer adhering to the surface, 37° *C. media* was added at 1:1 ratio to quench Trypsin, and the volume brought to 10 ml with media. The cells were resuspended in 10 mL media, and 406 µL of 37% formaldehyde added, and incubated at room temp for 10 minutes with gentle shaking. Eight hundred microliters of 2.5 M Glycine were added to the cells and incubated on ice for 5 minutes. The cells were centrifuged at 550×g for 8 minutes at 4° and washed with 10 mL of ice cold PBS. After resuspending the cells in 5 mL of ice cold NIB, they were incubated on ice for 20 minutes with gentle mixing.

The cells or nuclei from either suspension cell culture or adherent cell culture were pelleted by spinning at 500×g for 5 minutes and washed with 900 µL of 1×NEBuffer 2.1. After spinning at 500×g for 5 minutes, the pellet was resuspended in 800 µL 1×NEBuffer 2.1 with 12 µL of 20% SDS and incubated at 42° C. with vigorous shaking for 30 minutes, and then 200 µL of 10% Triton™ X-100 was added and incubated at 42° C. with vigorous shaking for 30 minutes. The cells were gently passed through a 35 µM cell strainer, and 5 µL DAPI (5 mg/mL) was added.

Example 4

Nuclei Sorting and Tagmentation

A tagmentation plate was prepared with 10 µL 1×TD buffer (for 1 plate: 500 µL NIB buffer+500 µL TD buffer), and 2500 single nuclei were sorted into each well of the tagmentation plate. At this step the number of nuclei per well can be varied slightly as long as the number of nuclei per well is consistent for the whole plate. It is also possible to multiplex different samples into different wells of the plate as the transposase index will be preserved. The cells were gated according to FIG. 2. After spinning down the plate at 500×g for 5 min, 4 µL 500 nM of uniquely indexed cytosine-depleted transposome were added to each well. After sealing, the plate was incubated at 55° C. for 15 minutes with gentle shaking. The plate was then placed on ice. All the wells were pooled, and then passed through a 35 µM cell strainer. Five microliters DAPI (5 mg/mL) were added.

Example 5

Second Sort of Nuclei

A master mix was prepared for each well with 5 uL Zymo Digestion Reagent (2.5 uL M-Digestion Buffer, 2.25 uL H2O, and 0.25 uL Proteinase K). Either 10 or 22 single nuclei were sorted into each well using the most stringent sort settings. Ten single nuclei were sorted into wells to be used for unmethylated control spike-ins, and 22 cells were sorted into the other wells. The plate is then spun down at 600×g for 5 min at 4° C.

Example 6

Digestion and Bisulfite Conversion

Approximately ~35 µg (2 µL) of Unmethylated Control Lambda DNA Pre-treated with a C-depleted transposome were used to spike the wells with 10 single nuclei. The plate was incubated for 20 minutes at 50° C. to digest nuclei, and 32.5 µL freshly prepared Zymo CT Conversion Reagent was added following the manufacturer's protocol. The wells were mixed by triturating, and the plate was spun down at 600×g for 2 min at 4° C. The plate was placed on a thermocycler for the following steps before continuing: 98° C. for 8 minutes, 64° C. for 3.5 hours, then hold at 4° C. for less than 20 hours. Zymo MagBinding Beads (5 µL) were added to each well, and 150 µL of M-Binding Buffer were added to each well. After mixing the wells by triturating, the plate was incubated at room temperature for 5 minutes. The plate was placed on a 96-well compatible magnetic rack until supernatant was clear.

The supernatant was removed and the wells were washed with fresh 80% Ethanol (by volume) by i) removing the plate from the magnetic rack, ii) adding 100 µL of 80% Ethanol to each well, running over bead pellet, and iii) placing the plate back on the magnetic rack and then removing the supernatant once clear.

Desulphonation was accomplished by adding 50 µL M-Desulphonation Buffer to each well, resuspending the beads fully by trituration, incubating at room temperature for 15 minutes, and placing the plate on the magnetic rack and then removing the supernatant once clear.

The supernatant was removed and the wells are washed with fresh 80% Ethanol (by volume) by i) removing the plate from the magnetic rack, ii) adding 100 µL of 80% Ethanol to each well, running over bead pellet, and iii) placing the plate back on the magnetic rack and then removing the supernatant once clear.

The bead pellets were allowed to dry for ~10 minutes until pellets began to visibly crack.

Elution was accomplished by adding 25 µL of Zymo M-Elution Buffer to each well, triturating to fully dissociate pellet, and heating the plate at 55° C. for 4 minutes.

Example 7

Linear Amplification

The full elution was moved to a plate prepared with the following reaction mix per well: 16 uL PCR-clean H2O, 5 uL 10X NEBuffer 2.1, 2 uL 10 mM dNTP Mix, and 2 uL 10 uM 9-Nucleotide Random Primer.

Linear amplification was performed as follows: i) render DNA single-stranded by incubating at 95° C. for 45 seconds, then flash cool on ice and hold on ice, ii. add 10U Klenow (3'->5' exo-) polymerase to each well once fully cooled, and iii) incubate plate at 4° C. for 5 minutes, then ramp temperature up at a rate of +1° C./15 sec to 37° C., then hold at 37° C. for 90 minutes.

Steps i-iii were repeated three more times for a total of four rounds of linear amplification. For each amplification, the following mixture was added to the reaction in each well: 1 uL 10 uM 9-Nucleotide Random Primer, 1 uL 10 mM dNTP Mix, and 1.25 uL 4X NEBuffer 2.1. Four rounds of linear amplification typically significantly increases the read alignment rate and library complexity compared to fewer rounds.

The wells were cleaned up using the prepared 18% PEG SPRI Bead Mixture at 1.1X (concentration by volume compared to well reaction volume) as follows. The plate was incubated for 5 minutes at room temperature, placed on the magnetic rack, and removed supernatant once clear. The bead pellets were washed with 50 uL 80% Ethanol. Any liquid remaining was removed and the bead pellet allowed to dry until beginning to crack. DNA was eluted in 21 uL 10 mM Tris-Cl (pH 8.5).

Example 8

Indexing PCR Reaction

The full elution was moved to a plate prepared with the following reaction mix per well:

2 uL of 10 uM i7 index PCR primer, 2 uL of 10 uM i5 index PCR primer, 25 uL of 2X KAPA HiFi™ HotStart ReadyMix, and 0.5 uL 100X SYBR® Green I. PCR amplification was performed on a real-time thermocycler with the following cycles: 95° C. for 2 minutes, (94° C. for 80 seconds, 65° C. for 30 seconds, 72° C. for 30 seconds), and the reaction was stopped once a majority of wells showed an inflection of measured SYBR® Green fluorescence. Inflection plateaus were observed between 16-21 PCR cycles for library preparations.

Example 9

Library Clean Up and Quantification

Libraries were cleaned per-well using the 18% PEG SPRI Bead Mixture at 0.8X (concentration by volume compared to well reaction volume) as follows. The plate was incubated for 5 minutes at room temperature, placed on the magnetic rack, and supernatant was removed once clear. The bead pellets were washed with 50 uL 80% ethanol. Any liquid remaining was removed and the bead pellet allowed to dry until beginning to crack. DNA was eluted in 25 uL 10 mM Tris-Cl (pH 8.5).

Libraries were pooled using 5 uL of each well, and 2 uL was used to quantify the concentration of DNA with dsDNA High Sensitivity Qubit® 2.0 Fluorometer, following manufacturer's protocol. The Qubit® readout was used to dilute library to ~4 ng/uL, and 1 µL was run on a High Sensitivity Bioanalyser 2100, following manufacturer's protocol. The library was then quantified for the 200 bp-1 kbp range to dilute the pool to 1 nM for Illumina Sequencing.

Example 10

Sequencing

A NextSeq® 500 was set up for a run as per manufacturer's instructions for a 1 nM sample except for the following changes. The library pool was loaded at a concentration of 0.9 pM and a total volume of 1.5 mL and deposited into cartridge position 10; custom primers were setup by diluting 9 µL of 100 µM stock sequencing primer 1 into a total of 1.5 mL of HT1 buffer into cartridge position 7, and 18 µL of each custom index sequencing primer at 100 µM stock concentrations to a total of 3 mL of HT1 buffer into cartridge position 9; the NextSeq® 500 was operated in standalone mode; the SCIseq custom chemistry recipe (Amini et al., 2014, *Nat. Genet.* 46, 1343-1349) was selected; dual index was selected; the appropriate number of read cycles was entered (150 recommended); 10 cycles for index 1 and 20 cycles for index 2; the custom checkbox for all reads and indices was selected.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of preparing a sequencing library for determining the methylation status of nucleic acids from a plurality of single cells, the method comprising:

(a) providing isolated nuclei from a plurality of cells;

(b) subjecting the isolated nuclei to a chemical treatment to generating nucleosome-depleted nuclei, while maintaining integrity of the isolated nuclei;

(c) distributing subsets of the nucleosome-depleted nuclei into a first plurality of compartments comprising a transposome complex, wherein the transposome complex in each compartment comprises a first index sequence that is different from first index sequences in the other compartments and a single sequencing primer;

(d) fragmenting nucleic acids in the subsets of nucleosome-depleted nuclei into a plurality of nucleic acid fragments and incorporating the first index sequences and the single sequencing primer into at least one strand of the nucleic acid fragments to generate indexed nuclei;

(e) combining the indexed nuclei to generate pooled indexed nuclei;

(f) distributing subsets of the pooled indexed nuclei into a second plurality of compartments and subjecting the indexed nuclei to treatment to identify methylated nucleotides and generate treated nucleic acid fragments;

(g) amplifying the treated nucleic acid fragments in each compartment by linear amplification with a plurality of primers comprising a universal nucleotide sequence at the 5' end, wherein the universal nucleotide sequence comprises a second sequencing primer, and a random nucleotide sequence at the 3' end to generate amplified fragment-adapter molecules, wherein the amplified fragment-adapter molecules comprise nucleotides originating from the transposome complex at one end and nucleotides originating from the second sequencing primers at the other end;

(h) incorporating a second index sequence into the amplified fragment-adapter molecules to generate dual-index fragment-adapter molecules, wherein the second index sequence in each compartment is different from second index sequences in the other compartments; and (i) combining the dual-index fragment-adapter molecules, thereby producing a sequencing library for determining the methylation status of nucleic acids from the plurality of single cells.

2. The method of claim 1, wherein the chemical treatment comprises a treatment with a chaotropic agent capable of disrupting nucleic acid-protein interactions.

3. The method of claim 2, wherein the chaotropic agent comprises lithium diiodosalicylate.

4. The method of claim 1, wherein the chemical treatment comprises a treatment with a detergent capable of disrupting nucleic acid-protein interactions.

5. The method of claim 4, wherein the detergent comprises sodium dodecyl sulfate (SDS).

6. The method of claim 5, wherein the cells are treated with a cross-linking agent prior to step (a).

7. The method of claim 6, wherein the cross-linking agent is formaldehyde.

8. The method of claim 1, wherein the subsets of the nucleosome-depleted nuclei comprise approximately equal numbers of nuclei.

9. The method of claim 8, wherein the subsets of the nucleosome-depleted nuclei comprise from 1 to about 2000 nuclei.

10. The method of claim 1, wherein the subsets of the pooled indexed nuclei comprise approximately equal numbers of nuclei.

11. The method of claim 10, wherein the subsets of the pooled indexed nuclei comprise from 1 to about 25 nuclei.

12. The method of claim 1, wherein the subsets of the pooled indexed nuclei include at least 10 times fewer nuclei than the subsets of the nucleosome-depleted nuclei.

13. The method of claim 1, wherein the first plurality of compartments or the second plurality of compartments is a multi-well plate.

14. The method of claim 1, wherein each of the transposome complexes comprises transposases and transposons, each of the transposons comprising a transferred strand, wherein the transferred strand does not comprise a cytosine residue.

15. The method of claim 1, further comprising an enrichment of target nucleic acids using a plurality of capture oligonucleotides having specificity for the target nucleic acids, wherein the capture oligonucleotides are immobilized on a surface of a solid substrate.

16. The method of claim 1, wherein the treatment to identify methylated nucleotides comprises bisulfite or hydrazine.

* * * * *

SEQUENCE LISTING

```
<160> NUMBER OF SEQ ID NOS: 132

<210> SEQ ID NO 1
<211> LENGTH: 60
<212> TYPE: DNA
<213> ORGANISM: artificial
<220> FEATURE:
<223> OTHER INFORMATION: Oligo

<400> SEQUENCE: 1

ggtgtagtgg gtttgggtta agaggaatgg tagagagggt gagatgtgta taagagacag     60


<210> SEQ ID NO 2
<211> LENGTH: 60
<212> TYPE: DNA
<213> ORGANISM: artificial
<220> FEATURE:
```

<223> OTHER INFORMATION: Oligo

<400> SEQUENCE: 2
ggtgtagtgg gtttggagta ggaagattgg tagagagggt gagatgtgta taagagacag 60

<210> SEQ ID NO 3
<211> LENGTH: 60
<212> TYPE: DNA
<213> ORGANISM: artificial
<220> FEATURE:
<223> OTHER INFORMATION: Oligo

<400> SEQUENCE: 3
ggtgtagtgg gtttgggaat taggtgttgg tagagagggt gagatgtgta taagagacag 60

<210> SEQ ID NO 4
<211> LENGTH: 60
<212> TYPE: DNA
<213> ORGANISM: artificial
<220> FEATURE:
<223> OTHER INFORMATION: Oligo

<400> SEQUENCE: 4
ggtgtagtgg gtttggggag attaatgtgg tagagagggt gagatgtgta taagagacag 60

<210> SEQ ID NO 5
<211> LENGTH: 60
<212> TYPE: DNA
<213> ORGANISM: artificial
<220> FEATURE:
<223> OTHER INFORMATION: Oligo

<400> SEQUENCE: 5
ggtgtagtgg gtttggtatt gtggaattgg tagagagggt gagatgtgta taagagacag 60

<210> SEQ ID NO 6
<211> LENGTH: 60
<212> TYPE: DNA
<213> ORGANISM: artificial
<220> FEATURE:
<223> OTHER INFORMATION: Oligo

<400> SEQUENCE: 6
ggtgtagtgg gtttggatat agatgattgg tagagagggt gagatgtgta taagagacag 60

<210> SEQ ID NO 7
<211> LENGTH: 60
<212> TYPE: DNA
<213> ORGANISM: artificial
<220> FEATURE:
<223> OTHER INFORMATION: Oligo

<400> SEQUENCE: 7
ggtgtagtgg gtttgggtaa gaggaattgg tagagagggt gagatgtgta taagagacag 60

<210> SEQ ID NO 8
<211> LENGTH: 60
<212> TYPE: DNA
<213> ORGANISM: artificial
<220> FEATURE:
<223> OTHER INFORMATION: Oligo

<400> SEQUENCE: 8
ggtgtagtgg gtttgggaga gttattgtgg tagagagggt gagatgtgta taagagacag 60

<210> SEQ ID NO 9
<211> LENGTH: 60
<212> TYPE: DNA
<213> ORGANISM: artificial
<220> FEATURE:
<223> OTHER INFORMATION: Oligo

<400> SEQUENCE: 9
ggtgtagtgg gtttggagtt agtgtgatgg tagagagggt gagatgtgta taagagacag 60

<210> SEQ ID NO 10
<211> LENGTH: 60
<212> TYPE: DNA
<213> ORGANISM: artificial
<220> FEATURE:
<223> OTHER INFORMATION: Oligo

<400> SEQUENCE: 10
ggtgtagtgg gtttgggata tagaatttgg tagagagggt gagatgtgta taagagacag 60

<210> SEQ ID NO 11
<211> LENGTH: 60
<212> TYPE: DNA
<213> ORGANISM: artificial
<220> FEATURE:
<223> OTHER INFORMATION: Oligo

<400> SEQUENCE: 11
ggtgtagtgg gtttggaagg aagtgaatgg tagagagggt gagatgtgta taagagacag 60

<210> SEQ ID NO 12
<211> LENGTH: 60
<212> TYPE: DNA
<213> ORGANISM: artificial
<220> FEATURE:
<223> OTHER INFORMATION: Oligo

<400> SEQUENCE: 12
ggtgtagtgg gtttggaata aggaaggtgg tagagagggt gagatgtgta taagagacag 60

<210> SEQ ID NO 13
<211> LENGTH: 60
<212> TYPE: DNA
<213> ORGANISM: artificial
<220> FEATURE:
<223> OTHER INFORMATION: Oligo

<400> SEQUENCE: 13
ggtgtagtgg gtttgggtat ggatatatgg tagagagggt gagatgtgta taagagacag 60

<210> SEQ ID NO 14
<211> LENGTH: 60
<212> TYPE: DNA
<213> ORGANISM: artificial
<220> FEATURE:
<223> OTHER INFORMATION: Oligo

<400> SEQUENCE: 14
ggtgtagtgg gtttggttag ataatgatgg tagagagggt gagatgtgta taagagacag 60

<210> SEQ ID NO 15
<211> LENGTH: 60
<212> TYPE: DNA
<213> ORGANISM: artificial
<220> FEATURE:
<223> OTHER INFORMATION: Oligo

<400> SEQUENCE: 15
ggtgtagtgg gtttggggtg ttgtaattgg tagagagggt gagatgtgta taagagacag 60

<210> SEQ ID NO 16
<211> LENGTH: 60
<212> TYPE: DNA
<213> ORGANISM: artificial
<220> FEATURE:
<223> OTHER INFORMATION: Oligo

<400> SEQUENCE: 16
ggtgtagtgg gtttgggaag tggagagtgg tagagagggt gagatgtgta taagagacag 60

<210> SEQ ID NO 17
<211> LENGTH: 60
<212> TYPE: DNA
<213> ORGANISM: artificial
<220> FEATURE:
<223> OTHER INFORMATION: Oligo

<400> SEQUENCE: 17
ggtgtagtgg gtttggttga gtggtagtgg tagagagggt gagatgtgta taagagacag 60

<210> SEQ ID NO 18
<211> LENGTH: 60
<212> TYPE: DNA
<213> ORGANISM: artificial
<220> FEATURE:
<223> OTHER INFORMATION: Oligo

<400> SEQUENCE: 18
ggtgtagtgg gtttgggata atggtgatgg tagagagggt gagatgtgta taagagacag 60

<210> SEQ ID NO 19
<211> LENGTH: 60
<212> TYPE: DNA
<213> ORGANISM: artificial
<220> FEATURE:
<223> OTHER INFORMATION: Oligo

<400> SEQUENCE: 19
ggtgtagtgg gtttgggtgt taatggatgg tagagagggt gagatgtgta taagagacag 60

<210> SEQ ID NO 20
<211> LENGTH: 60
<212> TYPE: DNA
<213> ORGANISM: artificial
<220> FEATURE:
<223> OTHER INFORMATION: Oligo

<400> SEQUENCE: 20
ggtgtagtgg gtttggtagg aatggtgtgg tagagagggt gagatgtgta taagagacag 60

<210> SEQ ID NO 21
<211> LENGTH: 60
<212> TYPE: DNA
<213> ORGANISM: artificial
<220> FEATURE:
<223> OTHER INFORMATION: Oligo

<400> SEQUENCE: 21
ggtgtagtgg gtttggatgt atggatatgg tagagagggt gagatgtgta taagagacag 60

<210> SEQ ID NO 22
<211> LENGTH: 60

<212> TYPE: DNA
<213> ORGANISM: artificial
<220> FEATURE:
<223> OTHER INFORMATION: Oligo

<400> SEQUENCE: 22
ggtgtagtgg gtttggtgat tgttggttgg tagagagggt gagatgtgta taagagacag 60

<210> SEQ ID NO 23
<211> LENGTH: 60
<212> TYPE: DNA
<213> ORGANISM: artificial
<220> FEATURE:
<223> OTHER INFORMATION: Oligo

<400> SEQUENCE: 23
ggtgtagtgg gtttggaaga gaattattgg tagagagggt gagatgtgta taagagacag 60

<210> SEQ ID NO 24
<211> LENGTH: 60
<212> TYPE: DNA
<213> ORGANISM: artificial
<220> FEATURE:
<223> OTHER INFORMATION: Oligo

<400> SEQUENCE: 24
ggtgtagtgg gtttggaatg gttggtatgg tagagagggt gagatgtgta taagagacag 60

<210> SEQ ID NO 25
<211> LENGTH: 60
<212> TYPE: DNA
<213> ORGANISM: artificial
<220> FEATURE:
<223> OTHER INFORMATION: Oligo

<400> SEQUENCE: 25
ggtgtagtgg gtttggggtt aattgagtgg tagagagggt gagatgtgta taagagacag 60

<210> SEQ ID NO 26
<211> LENGTH: 60
<212> TYPE: DNA
<213> ORGANISM: artificial
<220> FEATURE:
<223> OTHER INFORMATION: Oligo

<400> SEQUENCE: 26
ggtgtagtgg gtttgggtat aatagtttgg tagagagggt gagatgtgta taagagacag 60

<210> SEQ ID NO 27
<211> LENGTH: 60
<212> TYPE: DNA
<213> ORGANISM: artificial
<220> FEATURE:
<223> OTHER INFORMATION: Oligo

<400> SEQUENCE: 27
ggtgtagtgg gtttggttag ttgaatttgg tagagagggt gagatgtgta taagagacag 60

<210> SEQ ID NO 28
<211> LENGTH: 60
<212> TYPE: DNA
<213> ORGANISM: artificial
<220> FEATURE:
<223> OTHER INFORMATION: Oligo

<400> SEQUENCE: 28
ggtgtagtgg gtttggttgg tgaaggttgg tagagagggt gagatgtgta taagagacag 60

<210> SEQ ID NO 29
<211> LENGTH: 60
<212> TYPE: DNA
<213> ORGANISM: artificial
<220> FEATURE:
<223> OTHER INFORMATION: Oligo

<400> SEQUENCE: 29
ggtgtagtgg gtttggttaa tattgaatgg tagagagggt gagatgtgta taagagacag 60

<210> SEQ ID NO 30
<211> LENGTH: 60
<212> TYPE: DNA
<213> ORGANISM: artificial
<220> FEATURE:
<223> OTHER INFORMATION: Oligo

<400> SEQUENCE: 30
ggtgtagtgg gtttgggtta gaattggtgg tagagagggt gagatgtgta taagagacag 60

<210> SEQ ID NO 31
<211> LENGTH: 60
<212> TYPE: DNA
<213> ORGANISM: artificial
<220> FEATURE:
<223> OTHER INFORMATION: Oligo

<400> SEQUENCE: 31
ggtgtagtgg gtttgggtta ttaattatgg tagagagggt gagatgtgta taagagacag 60

<210> SEQ ID NO 32
<211> LENGTH: 60
<212> TYPE: DNA
<213> ORGANISM: artificial
<220> FEATURE:
<223> OTHER INFORMATION: Oligo

<400> SEQUENCE: 32
ggtgtagtgg gtttgggatt ggtaagatgg tagagagggt gagatgtgta taagagacag 60

<210> SEQ ID NO 33
<211> LENGTH: 60
<212> TYPE: DNA
<213> ORGANISM: artificial
<220> FEATURE:
<223> OTHER INFORMATION: Oligo

<400> SEQUENCE: 33
ggtgtagtgg gtttggtgaa gtattgttgg tagagagggt gagatgtgta taagagacag 60

<210> SEQ ID NO 34
<211> LENGTH: 60
<212> TYPE: DNA
<213> ORGANISM: artificial
<220> FEATURE:
<223> OTHER INFORMATION: Oligo

<400> SEQUENCE: 34
ggtgtagtgg gtttgggatg gattatgtgg tagagagggt gagatgtgta taagagacag 60

<210> SEQ ID NO 35
<211> LENGTH: 60
<212> TYPE: DNA
<213> ORGANISM: artificial

<220> FEATURE:
<223> OTHER INFORMATION: Oligo

<400> SEQUENCE: 35
ggtgtagtgg gtttggatta gtatatttgg tagagagggt gagatgtgta taagagacag 60

<210> SEQ ID NO 36
<211> LENGTH: 60
<212> TYPE: DNA
<213> ORGANISM: artificial
<220> FEATURE:
<223> OTHER INFORMATION: Oligo

<400> SEQUENCE: 36
ggtgtagtgg gtttgggtag gtgtggttgg tagagagggt gagatgtgta taagagacag 60

<210> SEQ ID NO 37
<211> LENGTH: 60
<212> TYPE: DNA
<213> ORGANISM: artificial
<220> FEATURE:
<223> OTHER INFORMATION: Oligo

<400> SEQUENCE: 37
ggtgtagtgg gtttggagtt gaatgtatgg tagagagggt gagatgtgta taagagacag 60

<210> SEQ ID NO 38
<211> LENGTH: 60
<212> TYPE: DNA
<213> ORGANISM: artificial
<220> FEATURE:
<223> OTHER INFORMATION: Oligo

<400> SEQUENCE: 38
ggtgtagtgg gtttggattg tgagatatgg tagagagggt gagatgtgta taagagacag 60

<210> SEQ ID NO 39
<211> LENGTH: 60
<212> TYPE: DNA
<213> ORGANISM: artificial
<220> FEATURE:
<223> OTHER INFORMATION: Oligo

<400> SEQUENCE: 39
ggtgtagtgg gtttggttgt ggtgagttgg tagagagggt gagatgtgta taagagacag 60

<210> SEQ ID NO 40
<211> LENGTH: 60
<212> TYPE: DNA
<213> ORGANISM: artificial
<220> FEATURE:
<223> OTHER INFORMATION: Oligo

<400> SEQUENCE: 40
ggtgtagtgg gtttggttaa gttggtttgg tagagagggt gagatgtgta taagagacag 60

<210> SEQ ID NO 41
<211> LENGTH: 60
<212> TYPE: DNA
<213> ORGANISM: artificial
<220> FEATURE:
<223> OTHER INFORMATION: Oligo

<400> SEQUENCE: 41
ggtgtagtgg gtttggtata ataatattgg tagagagggt gagatgtgta taagagacag 60

<210> SEQ ID NO 42
<211> LENGTH: 60
<212> TYPE: DNA
<213> ORGANISM: artificial
<220> FEATURE:
<223> OTHER INFORMATION: Oligo

<400> SEQUENCE: 42
ggtgtagtgg gtttggaagg tatgagttgg tagagagggt gagatgtgta taagagacag 60

<210> SEQ ID NO 43
<211> LENGTH: 60
<212> TYPE: DNA
<213> ORGANISM: artificial
<220> FEATURE:
<223> OTHER INFORMATION: Oligo

<400> SEQUENCE: 43
ggtgtagtgg gtttggagga ttataagtgg tagagagggt gagatgtgta taagagacag 60

<210> SEQ ID NO 44
<211> LENGTH: 60
<212> TYPE: DNA
<213> ORGANISM: artificial
<220> FEATURE:
<223> OTHER INFORMATION: Oligo

<400> SEQUENCE: 44
ggtgtagtgg gtttggagag ttaggtttgg tagagagggt gagatgtgta taagagacag 60

<210> SEQ ID NO 45
<211> LENGTH: 60
<212> TYPE: DNA
<213> ORGANISM: artificial
<220> FEATURE:
<223> OTHER INFORMATION: Oligo

<400> SEQUENCE: 45
ggtgtagtgg gtttggatgg atagtattgg tagagagggt gagatgtgta taagagacag 60

<210> SEQ ID NO 46
<211> LENGTH: 60
<212> TYPE: DNA
<213> ORGANISM: artificial
<220> FEATURE:
<223> OTHER INFORMATION: Oligo

<400> SEQUENCE: 46
ggtgtagtgg gtttggatat tatgttgtgg tagagagggt gagatgtgta taagagacag 60

<210> SEQ ID NO 47
<211> LENGTH: 60
<212> TYPE: DNA
<213> ORGANISM: artificial
<220> FEATURE:
<223> OTHER INFORMATION: Oligo

<400> SEQUENCE: 47
ggtgtagtgg gtttggggtg gagatagtgg tagagagggt gagatgtgta taagagacag 60

<210> SEQ ID NO 48
<211> LENGTH: 60
<212> TYPE: DNA
<213> ORGANISM: artificial
<220> FEATURE:
<223> OTHER INFORMATION: Oligo

<400> SEQUENCE: 48
ggtgtagtgg gtttggtggt ggtagtgtgg tagagagggt gagatgtgta taagagacag 60

<210> SEQ ID NO 49
<211> LENGTH: 60
<212> TYPE: DNA
<213> ORGANISM: artificial
<220> FEATURE:
<223> OTHER INFORMATION: Oligo

<400> SEQUENCE: 49
ggtgtagtgg gtttggaggt gagaagttgg tagagagggt gagatgtgta taagagacag 60

<210> SEQ ID NO 50
<211> LENGTH: 60
<212> TYPE: DNA
<213> ORGANISM: artificial
<220> FEATURE:
<223> OTHER INFORMATION: Oligo

<400> SEQUENCE: 50
ggtgtagtgg gtttggtagg aggttgttgg tagagagggt gagatgtgta taagagacag 60

<210> SEQ ID NO 51
<211> LENGTH: 60
<212> TYPE: DNA
<213> ORGANISM: artificial
<220> FEATURE:
<223> OTHER INFORMATION: Oligo

<400> SEQUENCE: 51
ggtgtagtgg gtttggtgta taggtattgg tagagagggt gagatgtgta taagagacag 60

<210> SEQ ID NO 52
<211> LENGTH: 60
<212> TYPE: DNA
<213> ORGANISM: artificial
<220> FEATURE:
<223> OTHER INFORMATION: Oligo

<400> SEQUENCE: 52
ggtgtagtgg gtttggtgtt atgtagatgg tagagagggt gagatgtgta taagagacag 60

<210> SEQ ID NO 53
<211> LENGTH: 60
<212> TYPE: DNA
<213> ORGANISM: artificial
<220> FEATURE:
<223> OTHER INFORMATION: Oligo

<400> SEQUENCE: 53
ggtgtagtgg gtttggtgga aggtatgtgg tagagagggt gagatgtgta taagagacag 60

<210> SEQ ID NO 54
<211> LENGTH: 60
<212> TYPE: DNA
<213> ORGANISM: artificial
<220> FEATURE:
<223> OTHER INFORMATION: Oligo

<400> SEQUENCE: 54
ggtgtagtgg gtttggaatg taaggagtgg tagagagggt gagatgtgta taagagacag 60

<210> SEQ ID NO 55

<211> LENGTH: 60
<212> TYPE: DNA
<213> ORGANISM: artificial
<220> FEATURE:
<223> OTHER INFORMATION: Oligo

<400> SEQUENCE: 55
ggtgtagtgg gtttgggtta tgttaagtgg tagagagggt gagatgtgta taagagacag 60

<210> SEQ ID NO 56
<211> LENGTH: 60
<212> TYPE: DNA
<213> ORGANISM: artificial
<220> FEATURE:
<223> OTHER INFORMATION: Oligo

<400> SEQUENCE: 56
ggtgtagtgg gtttggtgtt ataggtgtgg tagagagggt gagatgtgta taagagacag 60

<210> SEQ ID NO 57
<211> LENGTH: 60
<212> TYPE: DNA
<213> ORGANISM: artificial
<220> FEATURE:
<223> OTHER INFORMATION: Oligo

<400> SEQUENCE: 57
ggtgtagtgg gtttggaagg agaattgtgg tagagagggt gagatgtgta taagagacag 60

<210> SEQ ID NO 58
<211> LENGTH: 60
<212> TYPE: DNA
<213> ORGANISM: artificial
<220> FEATURE:
<223> OTHER INFORMATION: Oligo

<400> SEQUENCE: 58
ggtgtagtgg gtttggagag gtggaagtgg tagagagggt gagatgtgta taagagacag 60

<210> SEQ ID NO 59
<211> LENGTH: 60
<212> TYPE: DNA
<213> ORGANISM: artificial
<220> FEATURE:
<223> OTHER INFORMATION: Oligo

<400> SEQUENCE: 59
ggtgtagtgg gtttgggatt aggtgtatgg tagagagggt gagatgtgta taagagacag 60

<210> SEQ ID NO 60
<211> LENGTH: 60
<212> TYPE: DNA
<213> ORGANISM: artificial
<220> FEATURE:
<223> OTHER INFORMATION: Oligo

<400> SEQUENCE: 60
ggtgtagtgg gtttggatta tataagatgg tagagagggt gagatgtgta taagagacag 60

<210> SEQ ID NO 61
<211> LENGTH: 60
<212> TYPE: DNA
<213> ORGANISM: artificial
<220> FEATURE:
<223> OTHER INFORMATION: Oligo

<400> SEQUENCE: 61
ggtgtagtgg gtttgggaga atatggttgg tagagagggt gagatgtgta taagagacag 60

<210> SEQ ID NO 62
<211> LENGTH: 60
<212> TYPE: DNA
<213> ORGANISM: artificial
<220> FEATURE:
<223> OTHER INFORMATION: Oligo

<400> SEQUENCE: 62
ggtgtagtgg gtttggggat tgagaggtgg tagagagggt gagatgtgta taagagacag 60

<210> SEQ ID NO 63
<211> LENGTH: 60
<212> TYPE: DNA
<213> ORGANISM: artificial
<220> FEATURE:
<223> OTHER INFORMATION: Oligo

<400> SEQUENCE: 63
ggtgtagtgg gtttggatta tggtggttgg tagagagggt gagatgtgta taagagacag 60

<210> SEQ ID NO 64
<211> LENGTH: 60
<212> TYPE: DNA
<213> ORGANISM: artificial
<220> FEATURE:
<223> OTHER INFORMATION: Oligo

<400> SEQUENCE: 64
ggtgtagtgg gtttgggaag gaagttatgg tagagagggt gagatgtgta taagagacag 60

<210> SEQ ID NO 65
<211> LENGTH: 60
<212> TYPE: DNA
<213> ORGANISM: artificial
<220> FEATURE:
<223> OTHER INFORMATION: Oligo

<400> SEQUENCE: 65
ggtgtagtgg gtttgggaat atgtaagtgg tagagagggt gagatgtgta taagagacag 60

<210> SEQ ID NO 66
<211> LENGTH: 60
<212> TYPE: DNA
<213> ORGANISM: artificial
<220> FEATURE:
<223> OTHER INFORMATION: Oligo

<400> SEQUENCE: 66
ggtgtagtgg gtttggtagt taatatttgg tagagagggt gagatgtgta taagagacag 60

<210> SEQ ID NO 67
<211> LENGTH: 60
<212> TYPE: DNA
<213> ORGANISM: artificial
<220> FEATURE:
<223> OTHER INFORMATION: Oligo

<400> SEQUENCE: 67
ggtgtagtgg gtttggtgaa tgaatagtgg tagagagggt gagatgtgta taagagacag 60

<210> SEQ ID NO 68
<211> LENGTH: 60
<212> TYPE: DNA

<213> ORGANISM: artificial
<220> FEATURE:
<223> OTHER INFORMATION: Oligo

<400> SEQUENCE: 68
ggtgtagtgg gtttggagga tggattatgg tagagagggt gagatgtgta taagagacag 60

<210> SEQ ID NO 69
<211> LENGTH: 60
<212> TYPE: DNA
<213> ORGANISM: artificial
<220> FEATURE:
<223> OTHER INFORMATION: Oligo

<400> SEQUENCE: 69
ggtgtagtgg gtttggaagt gtatagatgg tagagagggt gagatgtgta taagagacag 60

<210> SEQ ID NO 70
<211> LENGTH: 60
<212> TYPE: DNA
<213> ORGANISM: artificial
<220> FEATURE:
<223> OTHER INFORMATION: Oligo

<400> SEQUENCE: 70
ggtgtagtgg gtttgggagg ttgaagatgg tagagagggt gagatgtgta taagagacag 60

<210> SEQ ID NO 71
<211> LENGTH: 60
<212> TYPE: DNA
<213> ORGANISM: artificial
<220> FEATURE:
<223> OTHER INFORMATION: Oligo

<400> SEQUENCE: 71
ggtgtagtgg gtttggtgtg taataggtgg tagagagggt gagatgtgta taagagacag 60

<210> SEQ ID NO 72
<211> LENGTH: 60
<212> TYPE: DNA
<213> ORGANISM: artificial
<220> FEATURE:
<223> OTHER INFORMATION: Oligo

<400> SEQUENCE: 72
ggtgtagtgg gtttggttga ttagagatgg tagagagggt gagatgtgta taagagacag 60

<210> SEQ ID NO 73
<211> LENGTH: 60
<212> TYPE: DNA
<213> ORGANISM: artificial
<220> FEATURE:
<223> OTHER INFORMATION: Oligo

<400> SEQUENCE: 73
ggtgtagtgg gtttggtatg tgtgtggtgg tagagagggt gagatgtgta taagagacag 60

<210> SEQ ID NO 74
<211> LENGTH: 60
<212> TYPE: DNA
<213> ORGANISM: artificial
<220> FEATURE:
<223> OTHER INFORMATION: Oligo

<400> SEQUENCE: 74
ggtgtagtgg gtttgggaga tgagaattgg tagagagggt gagatgtgta taagagacag 60

<210> SEQ ID NO 75
<211> LENGTH: 60
<212> TYPE: DNA
<213> ORGANISM: artificial
<220> FEATURE:
<223> OTHER INFORMATION: Oligo

<400> SEQUENCE: 75
ggtgtagtgg gtttggtggt gaagtgatgg tagagagggt gagatgtgta taagagacag 60

<210> SEQ ID NO 76
<211> LENGTH: 60
<212> TYPE: DNA
<213> ORGANISM: artificial
<220> FEATURE:
<223> OTHER INFORMATION: Oligo

<400> SEQUENCE: 76
ggtgtagtgg gtttgggtgg taggatgtgg tagagagggt gagatgtgta taagagacag 60

<210> SEQ ID NO 77
<211> LENGTH: 60
<212> TYPE: DNA
<213> ORGANISM: artificial
<220> FEATURE:
<223> OTHER INFORMATION: Oligo

<400> SEQUENCE: 77
ggtgtagtgg gtttggtgta ggtgatatgg tagagagggt gagatgtgta taagagacag 60

<210> SEQ ID NO 78
<211> LENGTH: 60
<212> TYPE: DNA
<213> ORGANISM: artificial
<220> FEATURE:
<223> OTHER INFORMATION: Oligo

<400> SEQUENCE: 78
ggtgtagtgg gtttgggtaa ggtgtgatgg tagagagggt gagatgtgta taagagacag 60

<210> SEQ ID NO 79
<211> LENGTH: 60
<212> TYPE: DNA
<213> ORGANISM: artificial
<220> FEATURE:
<223> OTHER INFORMATION: Oligo

<400> SEQUENCE: 79
ggtgtagtgg gtttggagaa gagagtgtgg tagagagggt gagatgtgta taagagacag 60

<210> SEQ ID NO 80
<211> LENGTH: 60
<212> TYPE: DNA
<213> ORGANISM: artificial
<220> FEATURE:
<223> OTHER INFORMATION: Oligo

<400> SEQUENCE: 80
ggtgtagtgg gtttggggat gttgtattgg tagagagggt gagatgtgta taagagacag 60

<210> SEQ ID NO 81
<211> LENGTH: 60
<212> TYPE: DNA
<213> ORGANISM: artificial
<220> FEATURE:

<223> OTHER INFORMATION: Oligo

<400> SEQUENCE: 81
ggtgtagtgg gtttggaagt tatataatgg tagagagggt gagatgtgta taagagacag 60

<210> SEQ ID NO 82
<211> LENGTH: 60
<212> TYPE: DNA
<213> ORGANISM: artificial
<220> FEATURE:
<223> OTHER INFORMATION: Oligo

<400> SEQUENCE: 82
ggtgtagtgg gtttggtgga attaagttgg tagagagggt gagatgtgta taagagacag 60

<210> SEQ ID NO 83
<211> LENGTH: 60
<212> TYPE: DNA
<213> ORGANISM: artificial
<220> FEATURE:
<223> OTHER INFORMATION: Oligo

<400> SEQUENCE: 83
ggtgtagtgg gtttggtaat gagaggatgg tagagagggt gagatgtgta taagagacag 60

<210> SEQ ID NO 84
<211> LENGTH: 60
<212> TYPE: DNA
<213> ORGANISM: artificial
<220> FEATURE:
<223> OTHER INFORMATION: Oligo

<400> SEQUENCE: 84
ggtgtagtgg gtttggataa ttgatggtgg tagagagggt gagatgtgta taagagacag 60

<210> SEQ ID NO 85
<211> LENGTH: 60
<212> TYPE: DNA
<213> ORGANISM: artificial
<220> FEATURE:
<223> OTHER INFORMATION: Oligo

<400> SEQUENCE: 85
ggtgtagtgg gtttggtgtg aagagtatgg tagagagggt gagatgtgta taagagacag 60

<210> SEQ ID NO 86
<211> LENGTH: 60
<212> TYPE: DNA
<213> ORGANISM: artificial
<220> FEATURE:
<223> OTHER INFORMATION: Oligo

<400> SEQUENCE: 86
ggtgtagtgg gtttgggatg aatatgttgg tagagagggt gagatgtgta taagagacag 60

<210> SEQ ID NO 87
<211> LENGTH: 60
<212> TYPE: DNA
<213> ORGANISM: artificial
<220> FEATURE:
<223> OTHER INFORMATION: Oligo

<400> SEQUENCE: 87
ggtgtagtgg gtttggtgag gatagattgg tagagagggt gagatgtgta taagagacag 60

<210> SEQ ID NO 88
<211> LENGTH: 60
<212> TYPE: DNA
<213> ORGANISM: artificial
<220> FEATURE:
<223> OTHER INFORMATION: Oligo

<400> SEQUENCE: 88
ggtgtagtgg gtttggatta attagagtgg tagagagggt gagatgtgta taagagacag 60

<210> SEQ ID NO 89
<211> LENGTH: 60
<212> TYPE: DNA
<213> ORGANISM: artificial
<220> FEATURE:
<223> OTHER INFORMATION: Oligo

<400> SEQUENCE: 89
ggtgtagtgg gtttggggag agatggatgg tagagagggt gagatgtgta taagagacag 60

<210> SEQ ID NO 90
<211> LENGTH: 60
<212> TYPE: DNA
<213> ORGANISM: artificial
<220> FEATURE:
<223> OTHER INFORMATION: Oligo

<400> SEQUENCE: 90
ggtgtagtgg gtttggtaat tgaggaatgg tagagagggt gagatgtgta taagagacag 60

<210> SEQ ID NO 91
<211> LENGTH: 60
<212> TYPE: DNA
<213> ORGANISM: artificial
<220> FEATURE:
<223> OTHER INFORMATION: Oligo

<400> SEQUENCE: 91
ggtgtagtgg gtttggttgg aattaattgg tagagagggt gagatgtgta taagagacag 60

<210> SEQ ID NO 92
<211> LENGTH: 60
<212> TYPE: DNA
<213> ORGANISM: artificial
<220> FEATURE:
<223> OTHER INFORMATION: Oligo

<400> SEQUENCE: 92
ggtgtagtgg gtttggaatg ttattgttgg tagagagggt gagatgtgta taagagacag 60

<210> SEQ ID NO 93
<211> LENGTH: 60
<212> TYPE: DNA
<213> ORGANISM: artificial
<220> FEATURE:
<223> OTHER INFORMATION: Oligo

<400> SEQUENCE: 93
ggtgtagtgg gtttgggtag ttattagtgg tagagagggt gagatgtgta taagagacag 60

<210> SEQ ID NO 94
<211> LENGTH: 60
<212> TYPE: DNA
<213> ORGANISM: artificial
<220> FEATURE:
<223> OTHER INFORMATION: Oligo

<400> SEQUENCE: 94
ggtgtagtgg gtttggtata ttgtgagtgg tagagagggt gagatgtgta taagagacag 60

<210> SEQ ID NO 95
<211> LENGTH: 60
<212> TYPE: DNA
<213> ORGANISM: artificial
<220> FEATURE:
<223> OTHER INFORMATION: Oligo

<400> SEQUENCE: 95
ggtgtagtgg gtttgggtgt aggatagtgg tagagagggt gagatgtgta taagagacag 60

<210> SEQ ID NO 96
<211> LENGTH: 60
<212> TYPE: DNA
<213> ORGANISM: artificial
<220> FEATURE:
<223> OTHER INFORMATION: Oligo

<400> SEQUENCE: 96
ggtgtagtgg gtttggagag aagttggtgg tagagagggt gagatgtgta taagagacag 60

<210> SEQ ID NO 97
<211> LENGTH: 19
<212> TYPE: DNA
<213> ORGANISM: artificial
<220> FEATURE:
<223> OTHER INFORMATION: Oligo

<400> SEQUENCE: 97
ctgtctctta tacacatct 19

<210> SEQ ID NO 98
<211> LENGTH: 37
<212> TYPE: DNA
<213> ORGANISM: artificial
<220> FEATURE:
<223> OTHER INFORMATION: Random primer
<220> FEATURE:
<221> NAME/KEY: misc_feature
<222> LOCATION: (29)..(37)
<223> OTHER INFORMATION: n is a, c, g, or t

<400> SEQUENCE: 98
ggagttcaga cgtgtgctct tccgatctnn nnnnnnn 37

<210> SEQ ID NO 99
<211> LENGTH: 68
<212> TYPE: DNA
<213> ORGANISM: artificial
<220> FEATURE:
<223> OTHER INFORMATION: PCR Primer

<400> SEQUENCE: 99
caagcagaag acggcatacg agatcaagat gccggtgact ggagttcaga cgtgtgctct 60
tccgatct 68

<210> SEQ ID NO 100
<211> LENGTH: 68
<212> TYPE: DNA
<213> ORGANISM: artificial
<220> FEATURE:
<223> OTHER INFORMATION: PCR Primer

<400> SEQUENCE: 100
caagcagaag acggcatacg agataacgtc tagtgtgact ggagttcaga cgtgtgctct 60
tccgatct 68

<210> SEQ ID NO 101
<211> LENGTH: 68
<212> TYPE: DNA
<213> ORGANISM: artificial
<220> FEATURE:
<223> OTHER INFORMATION: PCR Primer

<400> SEQUENCE: 101
caagcagaag acggcatacg agataggtat actcgtgact ggagttcaga cgtgtgctct 60
tccgatct 68

<210> SEQ ID NO 102
<211> LENGTH: 68
<212> TYPE: DNA
<213> ORGANISM: artificial
<220> FEATURE:
<223> OTHER INFORMATION: PCR Primer

<400> SEQUENCE: 102
caagcagaag acggcatacg agatttcata ggacgtgact ggagttcaga cgtgtgctct 60
tccgatct 68

<210> SEQ ID NO 103
<211> LENGTH: 68
<212> TYPE: DNA
<213> ORGANISM: artificial
<220> FEATURE:
<223> OTHER INFORMATION: PCR Primer

<400> SEQUENCE: 103
caagcagaag acggcatacg agatggaggc ctccgtgact ggagttcaga cgtgtgctct 60
tccgatct 68

<210> SEQ ID NO 104
<211> LENGTH: 68
<212> TYPE: DNA
<213> ORGANISM: artificial
<220> FEATURE:
<223> OTHER INFORMATION: PCR Primer

<400> SEQUENCE: 104
caagcagaag acggcatacg agatttcaat ataagtgact ggagttcaga cgtgtgctct 60
tccgatct 68

<210> SEQ ID NO 105
<211> LENGTH: 68
<212> TYPE: DNA
<213> ORGANISM: artificial
<220> FEATURE:
<223> OTHER INFORMATION: PCR Primer

<400> SEQUENCE: 105
caagcagaag acggcatacg agatacgtca tatagtgact ggagttcaga cgtgtgctct 60
tccgatct 68

<210> SEQ ID NO 106
<211> LENGTH: 68
<212> TYPE: DNA

<213> ORGANISM: artificial
<220> FEATURE:
<223> OTHER INFORMATION: PCR Primer

<400> SEQUENCE: 106
caagcagaag acggcatacg agatttgacc aggagtgact ggagttcaga cgtgtgctct 60
tccgatct 68

<210> SEQ ID NO 107
<211> LENGTH: 68
<212> TYPE: DNA
<213> ORGANISM: artificial
<220> FEATURE:
<223> OTHER INFORMATION: PCR Primer

<400> SEQUENCE: 107
caagcagaag acggcatacg agatcggttg cgcggtgact ggagttcaga cgtgtgctct 60
tccgatct 68

<210> SEQ ID NO 108
<211> LENGTH: 68
<212> TYPE: DNA
<213> ORGANISM: artificial
<220> FEATURE:
<223> OTHER INFORMATION: PCR Primer

<400> SEQUENCE: 108
caagcagaag acggcatacg agatcaagga ggtcgtgact ggagttcaga cgtgtgctct 60
tccgatct 68

<210> SEQ ID NO 109
<211> LENGTH: 68
<212> TYPE: DNA
<213> ORGANISM: artificial
<220> FEATURE:
<223> OTHER INFORMATION: PCR Primer

<400> SEQUENCE: 109
caagcagaag acggcatacg agatttacga tgaagtgact ggagttcaga cgtgtgctct 60
tccgatct 68

<210> SEQ ID NO 110
<211> LENGTH: 68
<212> TYPE: DNA
<213> ORGANISM: artificial
<220> FEATURE:
<223> OTHER INFORMATION: PCR Primer

<400> SEQUENCE: 110
caagcagaag acggcatacg agatttgctg gcatgtgact ggagttcaga cgtgtgctct 60
tccgatct 68

<210> SEQ ID NO 111
<211> LENGTH: 68
<212> TYPE: DNA
<213> ORGANISM: artificial
<220> FEATURE:
<223> OTHER INFORMATION: PCR Primer

<400> SEQUENCE: 111
caagcagaag acggcatacg agataatact cttcgtgact ggagttcaga cgtgtgctct 60
tccgatct 68

<210> SEQ ID NO 112
<211> LENGTH: 68
<212> TYPE: DNA
<213> ORGANISM: artificial
<220> FEATURE:
<223> OTHER INFORMATION: PCR Primer

<400> SEQUENCE: 112
caagcagaag acggcatacg agatccaact aaccgtgact ggagttcaga cgtgtgctct 60
tccgatct 68

<210> SEQ ID NO 113
<211> LENGTH: 68
<212> TYPE: DNA
<213> ORGANISM: artificial
<220> FEATURE:
<223> OTHER INFORMATION: PCR Primer

<400> SEQUENCE: 113
caagcagaag acggcatacg agattatcct caatgtgact ggagttcaga cgtgtgctct 60
tccgatct 68

<210> SEQ ID NO 114
<211> LENGTH: 68
<212> TYPE: DNA
<213> ORGANISM: artificial
<220> FEATURE:
<223> OTHER INFORMATION: PCR Primer

<400> SEQUENCE: 114
caagcagaag acggcatacg agatgccgtc gcgtgtgact ggagttcaga cgtgtgctct 60
tccgatct 68

<210> SEQ ID NO 115
<211> LENGTH: 68
<212> TYPE: DNA
<213> ORGANISM: artificial
<220> FEATURE:
<223> OTHER INFORMATION: PCR Primer

<400> SEQUENCE: 115
caagcagaag acggcatacg agatccgctg cttcgtgact ggagttcaga cgtgtgctct 60
tccgatct 68

<210> SEQ ID NO 116
<211> LENGTH: 68
<212> TYPE: DNA
<213> ORGANISM: artificial
<220> FEATURE:
<223> OTHER INFORMATION: PCR Primer

<400> SEQUENCE: 116
caagcagaag acggcatacg agattgaccg aatcgtgact ggagttcaga cgtgtgctct 60
tccgatct 68

<210> SEQ ID NO 117
<211> LENGTH: 68
<212> TYPE: DNA
<213> ORGANISM: artificial
<220> FEATURE:
<223> OTHER INFORMATION: PCR Primer

<400> SEQUENCE: 117
caagcagaag acggcatacg agatgtctcc agaggtgact ggagttcaga cgtgtgctct 60
tccgatct 68

<210> SEQ ID NO 118
<211> LENGTH: 68
<212> TYPE: DNA
<213> ORGANISM: artificial
<220> FEATURE:
<223> OTHER INFORMATION: PCR Primer

<400> SEQUENCE: 118
caagcagaag acggcatacg agataatgct agtcgtgact ggagttcaga cgtgtgctct 60
tccgatct 68

<210> SEQ ID NO 119
<211> LENGTH: 68
<212> TYPE: DNA
<213> ORGANISM: artificial
<220> FEATURE:
<223> OTHER INFORMATION: PCR Primer

<400> SEQUENCE: 119
caagcagaag acggcatacg agatgacgac ctgcgtgact ggagttcaga cgtgtgctct 60
tccgatct 68

<210> SEQ ID NO 120
<211> LENGTH: 68
<212> TYPE: DNA
<213> ORGANISM: artificial
<220> FEATURE:
<223> OTHER INFORMATION: PCR Primer

<400> SEQUENCE: 120
caagcagaag acggcatacg agatagagcc agccgtgact ggagttcaga cgtgtgctct 60
tccgatct 68

<210> SEQ ID NO 121
<211> LENGTH: 68
<212> TYPE: DNA
<213> ORGANISM: artificial
<220> FEATURE:
<223> OTHER INFORMATION: PCR Primer

<400> SEQUENCE: 121
caagcagaag acggcatacg agatccaggc cgcagtgact ggagttcaga cgtgtgctct 60
tccgatct 68

<210> SEQ ID NO 122
<211> LENGTH: 68
<212> TYPE: DNA
<213> ORGANISM: artificial
<220> FEATURE:
<223> OTHER INFORMATION: PCR Primer

<400> SEQUENCE: 122
caagcagaag acggcatacg agatcaggta tggagtgact ggagttcaga cgtgtgctct 60
tccgatct 68

<210> SEQ ID NO 123
<211> LENGTH: 55

<212> TYPE: DNA
<213> ORGANISM: artificial
<220> FEATURE:
<223> OTHER INFORMATION: PCR Primer

<400> SEQUENCE: 123
aatgatacgg cgaccaccga gatctacacg tatcatcgag gtgtagtggg tttgg 55

<210> SEQ ID NO 124
<211> LENGTH: 55
<212> TYPE: DNA
<213> ORGANISM: artificial
<220> FEATURE:
<223> OTHER INFORMATION: PCR Primer

<400> SEQUENCE: 124
aatgatacgg cgaccaccga gatctacacc cgcgattatg gtgtagtggg tttgg 55

<210> SEQ ID NO 125
<211> LENGTH: 55
<212> TYPE: DNA
<213> ORGANISM: artificial
<220> FEATURE:
<223> OTHER INFORMATION: PCR Primer

<400> SEQUENCE: 125
aatgatacgg cgaccaccga gatctacaca ttcaggtacg gtgtagtggg tttgg 55

<210> SEQ ID NO 126
<211> LENGTH: 55
<212> TYPE: DNA
<213> ORGANISM: artificial
<220> FEATURE:
<223> OTHER INFORMATION: PCR Primer

<400> SEQUENCE: 126
aatgatacgg cgaccaccga gatctacaca tggaattggg gtgtagtggg tttgg 55

<210> SEQ ID NO 127
<211> LENGTH: 55
<212> TYPE: DNA
<213> ORGANISM: artificial
<220> FEATURE:
<223> OTHER INFORMATION: PCR Primer

<400> SEQUENCE: 127
aatgatacgg cgaccaccga gatctacacg acgaagcgtg gtgtagtggg tttgg 55

<210> SEQ ID NO 128
<211> LENGTH: 55
<212> TYPE: DNA
<213> ORGANISM: artificial
<220> FEATURE:
<223> OTHER INFORMATION: PCR Primer

<400> SEQUENCE: 128
aatgatacgg cgaccaccga gatctacacc ttgcagtagg gtgtagtggg tttgg 55

<210> SEQ ID NO 129
<211> LENGTH: 55
<212> TYPE: DNA
<213> ORGANISM: artificial
<220> FEATURE:
<223> OTHER INFORMATION: PCR Primer

<400> SEQUENCE: 129

-continued

```
aatgatacgg cgaccaccga gatctacacc ttggtaatgg gtgtagtggg tttgg         55


<210> SEQ ID NO 130
<211> LENGTH: 55
<212> TYPE: DNA
<213> ORGANISM: artificial
<220> FEATURE:
<223> OTHER INFORMATION: PCR Primer

<400> SEQUENCE: 130

aatgatacgg cgaccaccga gatctacacc aagtcgaccg gtgtagtggg tttgg         55


<210> SEQ ID NO 131
<211> LENGTH: 33
<212> TYPE: DNA
<213> ORGANISM: artificial
<220> FEATURE:
<223> OTHER INFORMATION: Sequencing Primer

<400> SEQUENCE: 131

tggtagagag ggtgagatgt gtataagaga tag                                 33


<210> SEQ ID NO 132
<211> LENGTH: 33
<212> TYPE: DNA
<213> ORGANISM: artificial
<220> FEATURE:
<223> OTHER INFORMATION: Sequencing Primer

<400> SEQUENCE: 132

ctatctctta tacacatctc accctctcta cca                                 33
```